(12) United States Patent
Lecomte et al.

(10) Patent No.: US 9,668,887 B2
(45) Date of Patent: *Jun. 6, 2017

(54) FOOT PROSTHESIS WITH RESILIENT MULTI-AXIAL ANKLE

(71) Applicant: Össur hf, Reykjavik (IS)

(72) Inventors: Christophe Guy Lecomte, Reykjavik (IS); Hjordis Thorhallsdottir, Akureyri (IS); Heidrun Gígja Ragnarsdottir, Reykjavik (IS); Arinbjörn Viggo Clausen, Reykjavik (IS)

(73) Assignee: Össur hf, Reykjavik (IS)

( * ) Notice: Subject to any disclaimer, the term of this patent is extended or adjusted under 35 U.S.C. 154(b) by 0 days.

This patent is subject to a terminal disclaimer.

(21) Appl. No.: 14/853,491

(22) Filed: Sep. 14, 2015

(65) Prior Publication Data
US 2016/0067059 A1    Mar. 10, 2016

Related U.S. Application Data

(63) Continuation of application No. 13/196,339, filed on Aug. 2, 2011, now Pat. No. 9,132,022, which is a
(Continued)

(51) Int. Cl.
*A61F 2/66* (2006.01)
*A61F 2/30* (2006.01)
*A61F 2/50* (2006.01)

(52) U.S. Cl.
CPC .............. *A61F 2/66* (2013.01); *A61F 2/6607* (2013.01); *A61F 2002/30434* (2013.01);
(Continued)

(58) Field of Classification Search
CPC ....................... A61F 2/66; A61F 2/6607; A61F 2002/30434; A61F 2/6614; A61F 2002/6621; A61F 2002/6628
See application file for complete search history.

(56) References Cited

U.S. PATENT DOCUMENTS

| 25,238 A | 8/1859 | Bly |
| 53,931 A | 4/1866 | Weston |

(Continued)

FOREIGN PATENT DOCUMENTS

| DE | 817186 | 10/1951 |
| DE | 834884 | 3/1952 |

(Continued)

OTHER PUBLICATIONS

Commercial Ad for College Park Venture Prosthetic Foot; http://www.college/park.com/assets/pdf/VentureInfoSheets.pdf, © 2003, and www.college/park.com/CPStore/ProductInfoVenture.asp; available before Aug. 15, 2003.
(Continued)

*Primary Examiner* — Alvin Stewart
(74) *Attorney, Agent, or Firm* — Knobbe, Martens, Olson & Bear, LLP

(57) ABSTRACT

The present foot prosthesis includes various structural features that provide the foot with advantageous rollover properties. In certain embodiments, the foot guides rollover toward the medial side. For example, an asymmetrical upper element and a correspondingly shaped resilient ankle member support more of the wearer's weight on the lateral side as the foot rolls over. In another embodiment, stiffeners added to the resilient ankle member increase the stiffness on the lateral side relative to the medial side. In certain other embodiments, the foot provides progressively increasing support from mid stance through toe off. For example, a gap between the resilient ankle member and the lower element closes during the later portion of the wearer's gait. The closing gap increases a contact area between the resilient ankle member and the lower element, providing progressively increasing support. In another embodiment, the foot includes a gap between a lower front edge of an attachment
(Continued)

adapter and the upper element. The gap may be filled with a resilient material.

13 Claims, 30 Drawing Sheets

Related U.S. Application Data continuation of application No. 12/509,010, filed on Jul. 24, 2009, now Pat. No. 7,998,221, which is a continuation of application No. 10/987,940, filed on Nov. 12, 2004, now Pat. No. 7,846,213, which is a continuation-in-part of application No. 10/944,436, filed on Sep. 17, 2004, now Pat. No. 7,347,877.

(60) Provisional application No. 60/575,142, filed on May 28, 2004.

(52) U.S. Cl.
CPC . *A61F 2002/5003* (2013.01); *A61F 2002/503* (2013.01); *A61F 2002/5007* (2013.01); *A61F 2002/5009* (2013.01); *A61F 2002/5055* (2013.01); *A61F 2002/665* (2013.01); *A61F 2002/6614* (2013.01); *A61F 2002/6621* (2013.01); *A61F 2002/6628* (2013.01); *A61F 2002/6642* (2013.01); *A61F 2002/6685* (2013.01); *A61F 2220/0041* (2013.01); *A61F 2250/0018* (2013.01); *A61F 2250/0029* (2013.01)

(56) References Cited

U.S. PATENT DOCUMENTS

| | | |
|---|---|---|
| 56,983 A | 8/1866 | Nicholas |
| 57,666 A | 9/1866 | Bly |
| 368,580 A | 8/1887 | Frees |
| 487,697 A | 12/1892 | Ehle |
| 534,198 A | 2/1895 | Chapman |
| 619,731 A | 2/1899 | Doerflinger et al. |
| 808,296 A | 12/1905 | Merrick |
| 809,876 A | 1/1906 | Wilkins |
| 817,340 A | 4/1906 | Rosenkranz |
| 2,183,076 A | 12/1939 | Kaiser |
| 2,197,093 A | 4/1940 | Campbell |
| 2,315,795 A | 4/1943 | Johnson et al. |
| 2,357,893 A | 9/1944 | Harrington |
| 2,594,945 A | 4/1952 | Lucas et al. |
| 2,692,392 A | 10/1954 | Bennington et al. |
| 2,731,645 A | 1/1956 | Woodall |
| 3,551,914 A | 1/1971 | Woodall |
| 3,784,988 A | 1/1974 | Trumpler |
| 3,874,004 A | 4/1975 | May |
| 3,894,437 A | 7/1975 | Hagy et al. |
| 4,007,497 A | 2/1977 | Haupt |
| 4,267,728 A | 5/1981 | Manley et al. |
| 4,360,931 A | 11/1982 | Hampton |
| 4,387,472 A | 6/1983 | Wilson |
| 4,416,293 A | 11/1983 | Anderson et al. |
| 4,547,913 A | 10/1985 | Phillips |
| 4,631,676 A | 12/1986 | Pugh |
| 4,718,913 A | 1/1988 | Voisin |
| 4,813,436 A | 3/1989 | Au |
| 4,814,661 A | 3/1989 | Ratzlaff et al. |
| 4,822,363 A | 4/1989 | Phillips |
| 4,858,621 A | 8/1989 | Franks |
| 4,892,553 A | 1/1990 | Prahl |
| 4,892,554 A | 1/1990 | Robinson |
| 4,959,073 A | 9/1990 | Merlette |
| 5,019,109 A | 5/1991 | Voisin |
| 5,037,444 A | 8/1991 | Phillips |
| 5,062,859 A | 11/1991 | Naeder |
| 5,112,356 A | 5/1992 | Harris et al. |
| 5,116,384 A | 5/1992 | Wilson et al. |
| 5,128,880 A | 7/1992 | White |
| 5,139,525 A | 8/1992 | Kristinsson |
| 5,156,631 A | 10/1992 | Merlette |
| 5,156,632 A | 10/1992 | Wellershaus |
| 5,181,932 A | 1/1993 | Phillips |
| 5,181,933 A | 1/1993 | Phillips |
| 5,219,365 A | 6/1993 | Sabolich |
| 5,237,520 A | 8/1993 | White |
| 5,253,656 A | 10/1993 | Rincoe et al. |
| 5,258,038 A | 11/1993 | Robinson et al. |
| 5,258,039 A | 11/1993 | Goh et al. |
| 5,290,319 A | 3/1994 | Phillips |
| 5,361,133 A | 11/1994 | Brown et al. |
| 5,376,133 A | 12/1994 | Gramnas |
| 5,376,141 A | 12/1994 | Phillips |
| 5,387,246 A | 2/1995 | Phillips |
| 5,388,591 A | 2/1995 | De Luca et al. |
| 5,408,873 A | 4/1995 | Schmidt et al. |
| 5,425,781 A | 6/1995 | Allard et al. |
| 5,443,522 A | 8/1995 | Hiemisch |
| 5,443,527 A | 8/1995 | Wilson |
| 5,443,529 A | 8/1995 | Phillips |
| 5,471,405 A | 11/1995 | Marsh |
| 5,474,087 A | 12/1995 | Nashner |
| 5,509,938 A | 4/1996 | Phillips |
| 5,514,185 A | 5/1996 | Phillips |
| 5,545,234 A | 8/1996 | Collier, Jr. |
| 5,549,711 A | 8/1996 | Bryant |
| 5,623,944 A | 4/1997 | Nashner |
| 5,653,767 A | 8/1997 | Allen et al. |
| 5,695,526 A | 12/1997 | Wilson |
| 5,695,527 A | 12/1997 | Allen |
| 5,701,686 A | 12/1997 | Berr et al. |
| 5,728,177 A | 3/1998 | Phillips |
| 5,753,931 A | 5/1998 | Borchers et al. |
| 5,766,264 A | 6/1998 | Lundt |
| 5,790,256 A | 8/1998 | Brown et al. |
| 5,800,569 A | 9/1998 | Phillips |
| 5,824,112 A | 10/1998 | Phillips |
| 5,885,229 A | 3/1999 | Yamato et al. |
| 5,897,594 A | 4/1999 | Martin et al. |
| 5,899,944 A | 5/1999 | Phillips |
| 5,941,913 A | 8/1999 | Woolnough et al. |
| 5,944,760 A | 8/1999 | Christensen |
| 5,957,870 A | 9/1999 | Yamato et al. |
| 5,957,981 A | 9/1999 | Gramnas |
| 5,993,488 A | 11/1999 | Phillips |
| 6,063,046 A | 5/2000 | Allum |
| 6,071,313 A | 6/2000 | Phillips |
| 6,099,572 A | 8/2000 | Mosler et al. |
| 6,120,547 A | 9/2000 | Christensen |
| 6,129,766 A | 10/2000 | Johnson et al. |
| 6,165,227 A | 12/2000 | Phillips |
| 6,187,052 B1 | 2/2001 | Molino et al. |
| 6,197,067 B1 | 3/2001 | Shorter et al. |
| 6,197,068 B1 | 3/2001 | Christensen |
| 6,205,230 B1 | 3/2001 | Sundman et al. |
| 6,206,934 B1 | 3/2001 | Phillips |
| 6,216,545 B1 | 4/2001 | Taylor |
| 6,231,527 B1 | 5/2001 | Sol |
| 6,241,776 B1 | 6/2001 | Christensen |
| 6,261,324 B1 | 7/2001 | Merlette |
| 6,280,479 B1 | 8/2001 | Phillips |
| 6,289,107 B1 | 9/2001 | Borchers et al. |
| 6,290,730 B1 | 9/2001 | Pitkin et al. |
| 6,331,893 B1 | 12/2001 | Brown et al. |
| 6,350,286 B1 | 2/2002 | Atkinson et al. |
| 6,387,134 B1 | 5/2002 | Parker et al. |
| 6,398,818 B1 | 6/2002 | Merlette et al. |
| 6,402,790 B1 | 6/2002 | Celebi |
| 6,443,993 B1 | 9/2002 | Koniuk |
| 6,443,995 B1 | 9/2002 | Townsend et al. |
| 6,546,356 B1 | 4/2003 | Genest |
| 6,596,029 B1 | 7/2003 | Gramnas |
| 6,602,295 B1 | 8/2003 | Doddroe et al. |
| 6,663,672 B1 | 12/2003 | Laghi |
| 6,663,673 B2 | 12/2003 | Christensen |
| 6,676,708 B1 | 1/2004 | Laghi |

(56) References Cited

U.S. PATENT DOCUMENTS

| | | |
|---|---|---|
| 6,699,295 B2 | 3/2004 | Lee et al. |
| 6,702,859 B1 | 3/2004 | Laghi |
| 6,702,860 B1 | 3/2004 | Laghi |
| 6,706,075 B1 | 3/2004 | Laghi |
| 6,712,860 B2 | 3/2004 | Rubie et al. |
| 6,718,656 B2 | 4/2004 | Houser et al. |
| 6,719,807 B2 | 4/2004 | Harris |
| 6,743,260 B2* | 6/2004 | Townsend ............... A61F 2/66 623/49 |
| 6,764,521 B2 | 7/2004 | Molino et al. |
| 6,764,522 B1 | 7/2004 | Cehn |
| 6,767,370 B1 | 7/2004 | Mosler et al. |
| 6,793,683 B1 | 9/2004 | Laghi |
| 6,797,009 B1 | 9/2004 | Laghi |
| 6,805,717 B2 | 10/2004 | Christensen |
| 6,807,869 B2 | 10/2004 | Farringdon et al. |
| 6,827,744 B1 | 12/2004 | Laghi |
| 6,855,170 B2 | 2/2005 | Gramnas |
| 6,869,451 B1 | 3/2005 | Laghi |
| 6,875,240 B1 | 4/2005 | Laghi |
| 6,875,241 B2 | 4/2005 | Christensen |
| 6,875,242 B2 | 4/2005 | Christensen |
| 6,899,737 B1 | 5/2005 | Phillips |
| 6,929,665 B2 | 8/2005 | Christensen |
| 6,936,074 B2 | 8/2005 | Townsend et al. |
| 6,942,704 B2 | 9/2005 | Sulprizio |
| 6,966,933 B2 | 11/2005 | Christensen |
| 6,969,408 B2 | 11/2005 | Lecomte et al. |
| 7,052,519 B1 | 5/2006 | Gramnas |
| 7,063,727 B2 | 6/2006 | Phillips et al. |
| 7,108,723 B2 | 9/2006 | Townsend et al. |
| 7,112,227 B2 | 9/2006 | Doddroe et al. |
| 7,169,190 B2 | 1/2007 | Phillips et al. |
| 7,172,630 B2 | 2/2007 | Christensen |
| 7,211,115 B2 | 5/2007 | Townsend et al. |
| 7,219,449 B1 | 5/2007 | Hoffberg et al. |
| 7,279,011 B2 | 10/2007 | Phillips |
| 7,318,504 B2 | 1/2008 | Vitale et al. |
| 7,337,680 B2 | 3/2008 | Kantro |
| 7,341,603 B2 | 3/2008 | Christensen |
| 7,347,877 B2* | 3/2008 | Clausen ............... A61F 2/66 623/52 |
| 7,354,456 B2 | 4/2008 | Phillips |
| 7,371,262 B2 | 5/2008 | Lecomte et al. |
| 7,419,509 B2 | 9/2008 | Christensen |
| 7,429,272 B2 | 9/2008 | Townsend et al. |
| 7,431,737 B2 | 10/2008 | Ragnarsdottir et al. |
| 7,462,201 B2 | 12/2008 | Christensen |
| 7,520,904 B2 | 4/2009 | Christensen |
| 7,531,006 B2 | 5/2009 | Clausen et al. |
| 7,572,299 B2 | 8/2009 | Christensen |
| 7,578,852 B2 | 8/2009 | Townsend et al. |
| 7,581,454 B2 | 9/2009 | Clausen et al. |
| 7,617,068 B2 | 11/2009 | Tadin et al. |
| 7,618,464 B2 | 11/2009 | Christensen |
| 7,637,659 B2 | 12/2009 | Liu et al. |
| 7,637,957 B2 | 12/2009 | Ragnarsdóttir et al. |
| 7,648,533 B2 | 1/2010 | Phillips et al. |
| 7,686,848 B2 | 3/2010 | Christensen |
| 7,727,285 B2 | 6/2010 | Christensen et al. |
| 7,771,488 B2 | 8/2010 | Asgeirsson et al. |
| 7,815,689 B2 | 10/2010 | Bedard et al. |
| 7,833,287 B2 | 11/2010 | Doddroe et al. |
| 7,846,213 B2* | 12/2010 | Lecomte ............... A61F 2/66 623/52 |
| 7,862,621 B2 | 1/2011 | Kloos et al. |
| 7,862,622 B2 | 1/2011 | Dunlap et al. |
| 7,867,285 B2 | 1/2011 | Clausen et al. |
| 7,891,258 B2 | 2/2011 | Clausen et al. |
| 7,926,363 B2 | 4/2011 | Miller et al. |
| 7,951,101 B2 | 5/2011 | Pusch |
| 7,998,221 B2* | 8/2011 | Lecomte ............... A61F 2/66 623/52 |
| 8,025,699 B2* | 9/2011 | Lecomte ............... A61F 2/66 623/52 |
| 8,048,172 B2 | 11/2011 | Jonsson et al. |
| 8,070,829 B2 | 12/2011 | Townsend et al. |
| 8,075,501 B2 | 12/2011 | Miller et al. |
| 8,109,014 B2 | 2/2012 | Miller et al. |
| 8,117,922 B2 | 2/2012 | Xia et al. |
| 8,261,611 B2 | 9/2012 | Kim et al. |
| 8,290,739 B2 | 10/2012 | Tadin et al. |
| 8,486,156 B2* | 7/2013 | Jonsson ............... A61F 2/66 623/53 |
| 8,500,825 B2 | 8/2013 | Christensen et al. |
| D689,505 S | 9/2013 | Convay et al. |
| 8,544,347 B1 | 10/2013 | Berme |
| 9,132,022 B2* | 9/2015 | Lecomte ............... A61F 2/66 |
| 2002/0040249 A1 | 4/2002 | Phillips |
| 2002/0082713 A1* | 6/2002 | Townsend ............... A61F 2/66 623/55 |
| 2002/0087216 A1* | 7/2002 | Atkinson ............... A61F 2/66 623/38 |
| 2002/0116072 A1 | 8/2002 | Rubie et al. |
| 2002/0128727 A1 | 9/2002 | Merlette et al. |
| 2002/0138923 A1 | 10/2002 | Shaffeeullah |
| 2002/0143408 A1* | 10/2002 | Townsend ............... A61F 2/60 623/55 |
| 2002/0183860 A1 | 12/2002 | Wilkinson et al. |
| 2003/0045944 A1 | 3/2003 | Mosler et al. |
| 2003/0093158 A1 | 5/2003 | Phillips et al. |
| 2003/0120353 A1 | 6/2003 | Christensen |
| 2003/0191540 A1 | 10/2003 | Townsend et al. |
| 2004/0064195 A1 | 4/2004 | Herr |
| 2004/0068327 A1* | 4/2004 | Christensen ............... A61F 2/66 623/52 |
| 2004/0112138 A1 | 6/2004 | Knirck et al. |
| 2004/0122529 A1 | 6/2004 | Townsend et al. |
| 2004/0181289 A1 | 9/2004 | Bedard et al. |
| 2004/0225376 A1* | 11/2004 | Townsend ............... A61F 2/66 623/52 |
| 2005/0033451 A1* | 2/2005 | Aigner ............... A61F 2/66 623/53 |
| 2005/0038524 A1* | 2/2005 | Jonsson ............... A61F 2/66 623/55 |
| 2005/0038525 A1* | 2/2005 | Doddroe ............... A61F 2/66 623/55 |
| 2005/0060045 A1 | 3/2005 | Smith et al. |
| 2005/0071017 A1* | 3/2005 | Lecomte ............... A61F 2/66 623/52 |
| 2005/0071018 A1* | 3/2005 | Phillips ............... A61F 2/66 623/52 |
| 2005/0097970 A1 | 5/2005 | Nurse |
| 2005/0107889 A1 | 5/2005 | Bedard et al. |
| 2005/0137717 A1 | 6/2005 | Gramnäs et al. |
| 2005/0203640 A1 | 9/2005 | Christensen |
| 2005/0216097 A1 | 9/2005 | Rifkin |
| 2005/0273179 A1* | 12/2005 | Townsend ............... A61F 2/60 623/52 |
| 2006/0069450 A1 | 3/2006 | McCarvill et al. |
| 2006/0167563 A1 | 7/2006 | Johnson et al. |
| 2006/0173555 A1* | 8/2006 | Harn ............... A61F 2/66 623/52 |
| 2006/0247794 A1 | 11/2006 | Doddroe et al. |
| 2007/0027557 A1 | 2/2007 | Jonsson et al. |
| 2007/0039205 A1 | 2/2007 | Erb et al. |
| 2007/0043582 A1 | 2/2007 | Peveto et al. |
| 2007/0100465 A1 | 5/2007 | Egan |
| 2007/0106395 A9* | 5/2007 | Clausen ............... A61F 2/66 623/52 |
| 2007/0213840 A1* | 9/2007 | Townsend ............... A61F 2/60 623/51 |
| 2007/0250178 A1 | 10/2007 | Wilson |
| 2008/0046096 A1 | 2/2008 | Bedard et al. |
| 2008/0188951 A1 | 8/2008 | Christensen et al. |
| 2009/0012630 A1 | 1/2009 | Mosler et al. |
| 2009/0076626 A1 | 3/2009 | Ochoa |
| 2009/0105845 A1 | 4/2009 | Curtis |
| 2009/0204231 A1 | 8/2009 | Bonacini |
| 2009/0222105 A1* | 9/2009 | Clausen ............... A61F 2/60 623/27 |

(56) References Cited

U.S. PATENT DOCUMENTS

| | | |
|---|---|---|
| 2009/0234463 A1 | 9/2009 | Wilson |
| 2009/0293641 A1 | 12/2009 | Clausen et al. |
| 2009/0306792 A1 | 12/2009 | Lecomte et al. |
| 2010/0004757 A1 | 1/2010 | Clausen et al. |
| 2010/0023135 A1 | 1/2010 | Rubie et al. |
| 2010/0324699 A1 | 12/2010 | Herr et al. |
| 2011/0146396 A1 | 6/2011 | Kim et al. |
| 2011/0251520 A1 | 10/2011 | Shieh et al. |
| 2011/0288448 A1 | 11/2011 | Sanders et al. |
| 2012/0010730 A1* | 1/2012 | Lecomte ............... A61F 2/66 623/55 |
| 2012/0023776 A1 | 2/2012 | Skaja et al. |
| 2012/0035509 A1 | 2/2012 | Wilson et al. |
| 2012/0151794 A1 | 6/2012 | Hansen et al. |
| 2012/0166091 A1 | 6/2012 | Kim et al. |
| 2012/0266648 A1 | 10/2012 | Berme et al. |
| 2013/0018282 A1 | 1/2013 | Mainini et al. |
| 2015/0374514 A1* | 12/2015 | Clausen ............... A61F 2/66 623/53 |

FOREIGN PATENT DOCUMENTS

| | | |
|---|---|---|
| DE | 838480 | 5/1952 |
| DE | 695224 | 11/1954 |
| DE | 024763 | 1/1955 |
| DE | 924230 | 2/1955 |
| DE | 832473 | 2/1957 |
| DE | 300043 | 4/1964 |
| DE | 1491182 | 7/1969 |
| DE | 1941762 | 3/1971 |
| DE | 298 20 904 | 4/1999 |
| DE | 299 12 832 | 12/2000 |
| EP | 0 401 864 | 9/1989 |
| EP | 0 940 129 | 11/1992 |
| EP | 1 149 568 | 10/2001 |
| FR | 661071 | 7/1929 |
| FR | 1213026 | 3/1960 |
| FR | 2 658 717 | 8/1991 |
| GB | 117547 | 8/1918 |
| GB | 120462 | 11/1918 |
| GB | 621576 | 4/1949 |
| GB | 625528 | 6/1949 |
| GB | 1371996 | 10/1974 |
| KR | 2001-0055393 | 7/2001 |
| SU | 1454449 A1 | 1/1989 |
| SU | 1600759 A1 | 10/1990 |
| SU | 1700759 A1 | 12/1991 |
| WO | WO 88-06431 | 9/1988 |
| WO | WO 93-04645 | 3/1993 |
| WO | WO 94-18914 | 9/1994 |
| WO | WO 96-04869 | 2/1996 |
| WO | WO 98-53769 | 12/1998 |
| WO | WO 99-52476 | 10/1999 |
| WO | WO 00-27317 | 5/2000 |
| WO | WO 02-02034 A1 | 1/2002 |
| WO | WO 02-051342 | 7/2002 |
| WO | WO 2004-032809 | 4/2004 |
| WO | WO 2004-093959 | 4/2004 |
| WO | WO 2005/018495 | 3/2005 |
| WO | WO 2005-041819 | 5/2005 |
| WO | WO 2005-048887 | 6/2005 |

OTHER PUBLICATIONS

English translation of Gernhardsson, SE 9400380/3 A, published Aug. 5, 1995.
English translation of IPOS, DE 299 12 832 U1, published Nov. 2000.
English translation of KR 2000-002059A, notification date of Jan. 15, 2000.
Freedom Innovations FS2000 LP product; http://www.freedom/innovations.com/html/details.html, © 2003; available before Aug. 15, 2003.
Freedom Innovations Runway product; http://www.fredom/innovations.com/product_details.asp?seriesid=2&prodid=11, © 2004; available before Dec. 18, 2003.
Hosmer Dorrance Corporation: the Quantum Foot (4 pages) (no date but published more than one year prior to Nov. 12, 2004).
International Search Report dated May 27, 2005 for PCT/US2004/025554 filed Aug. 6, 2004.
International Search Report dated Apr. 28, 2006 for PCT/US2005/017884 filed May 20, 2006.
Ohio Willow Wood Company: Carbon Copy System III brochure, 5 pages; believed to have been available prior to May, 2004.
OSSUR Allurion product; http://www.ossur.com/template1.asp?pageid=84 and product catalog pp. 146/149; available before Aug. 15, 2003.
OSSUR Elation product; http://www.ossur.com/template1.asp?pageid=263 and product catalog pp. 193/196; available before Aug. 15, 2003.
OSSUR Total Concept product, OSSUR Product Catalog 2001/2002, pp. 243/249.
Otto Bock, Axtion product; http://www.ottobockus.com/products/lower_limb_prosthetics/axtion.asp; believed to have been released May 2004.
The Quantum Foot (Hosmer Dorrace Corporation), no date but published more than one year prior to Nov. 12, 2004.
Kim De Roy, "Influence of alignment variations of a prosthetic foot on lower limb kinematics and plantar pressure during below knee amputee gait," available before Sep. 20, 2004 (with English Abstract) Abstract.
Apr. 25, 2011 International Search Report and Written Opinion for PCT Application No. PCT/US2011/26124 filed Feb. 24, 2011.

\* cited by examiner

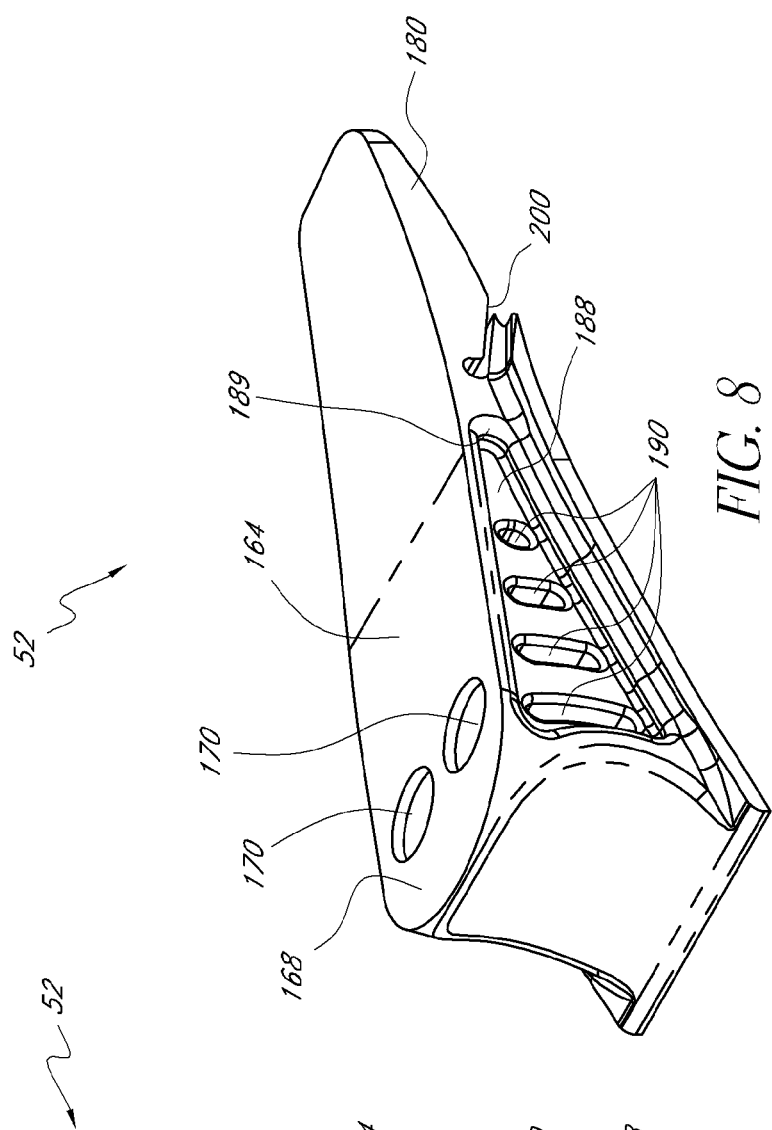
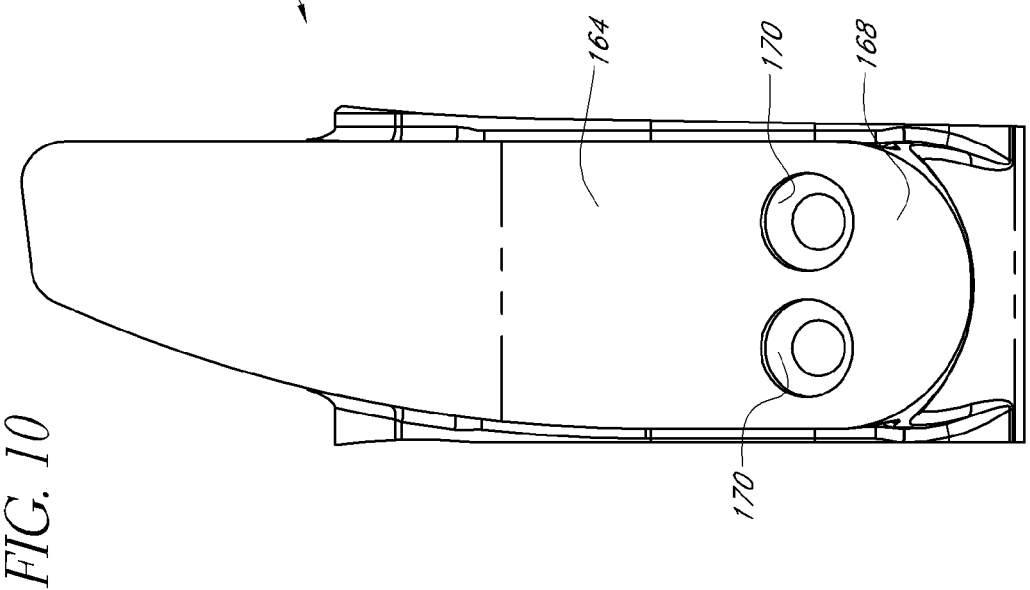

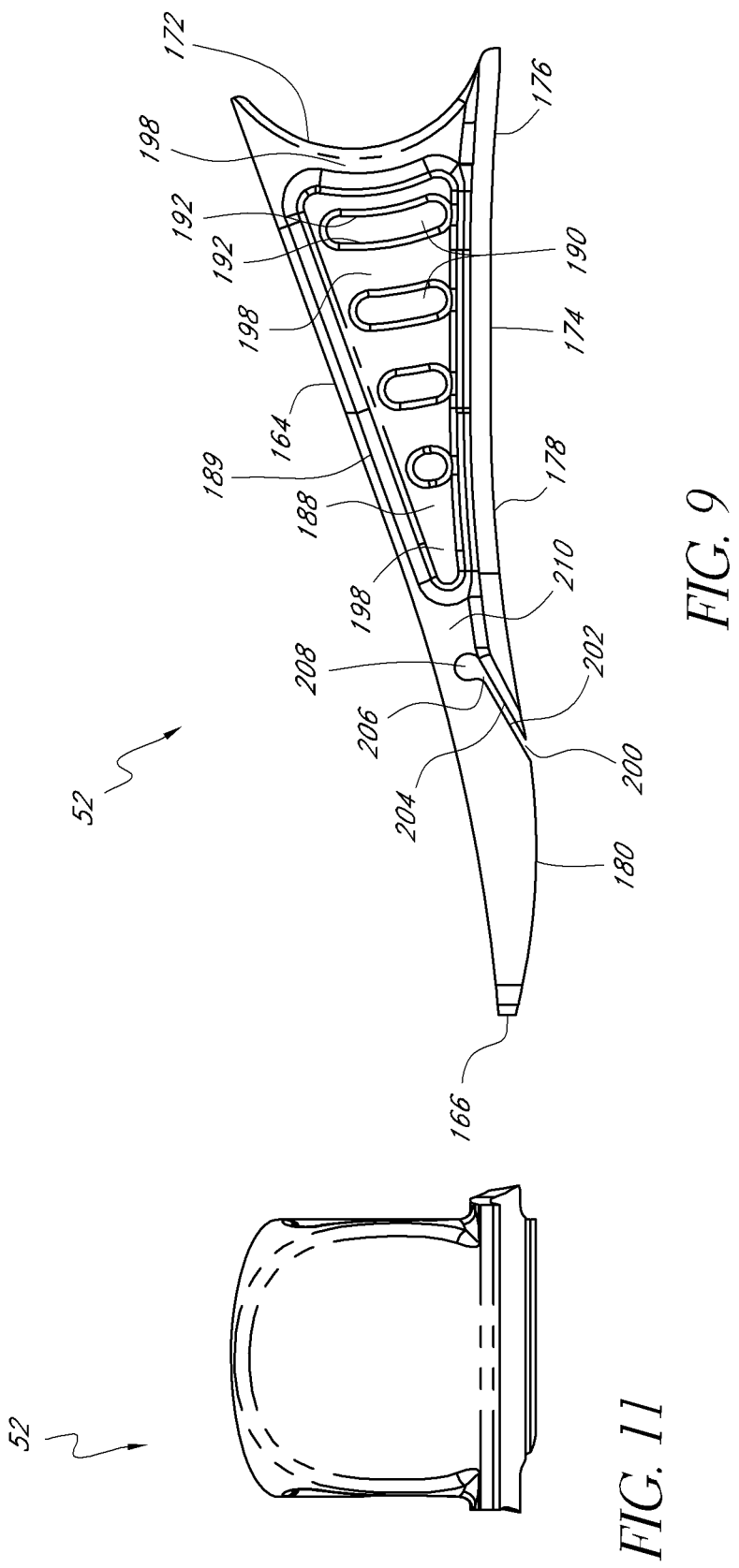

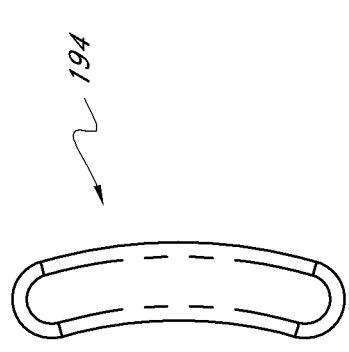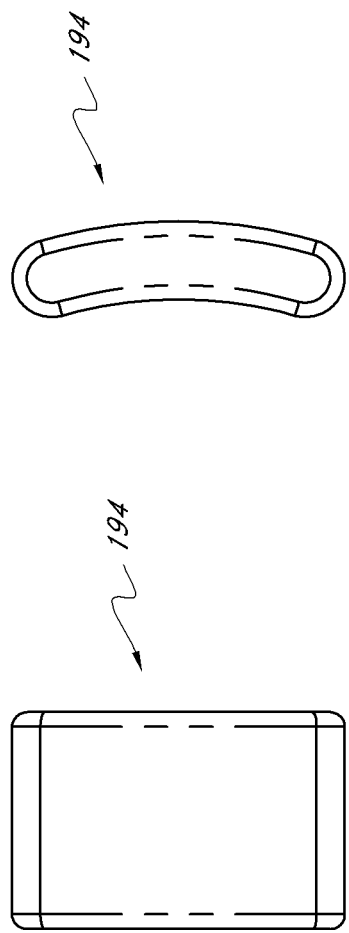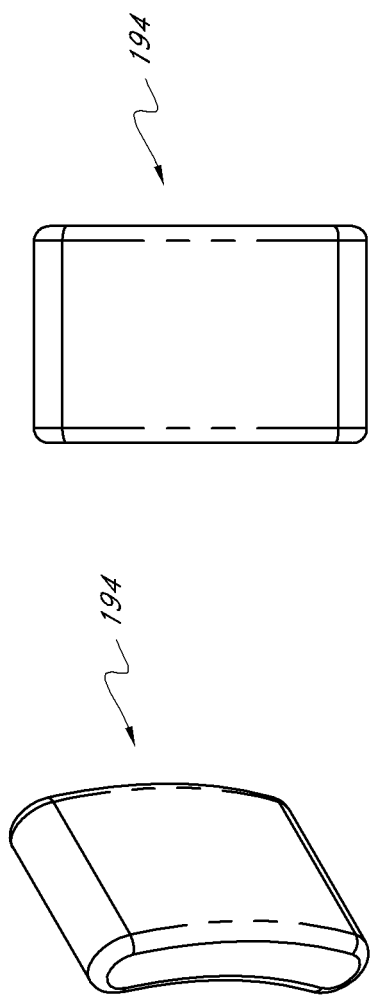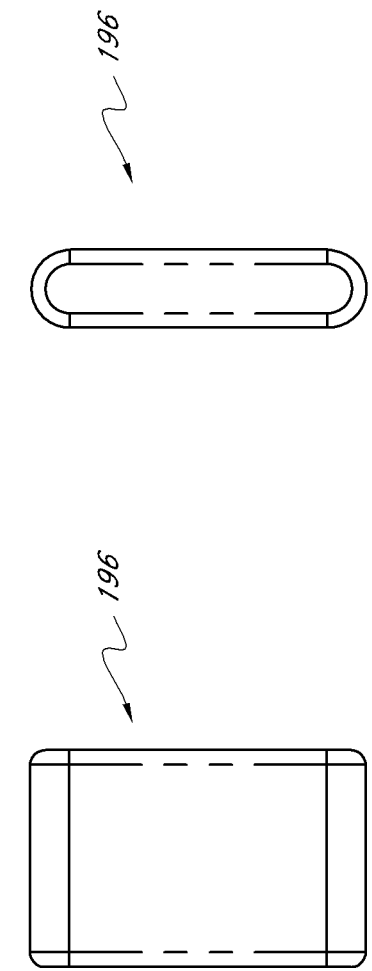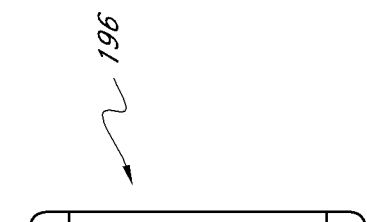

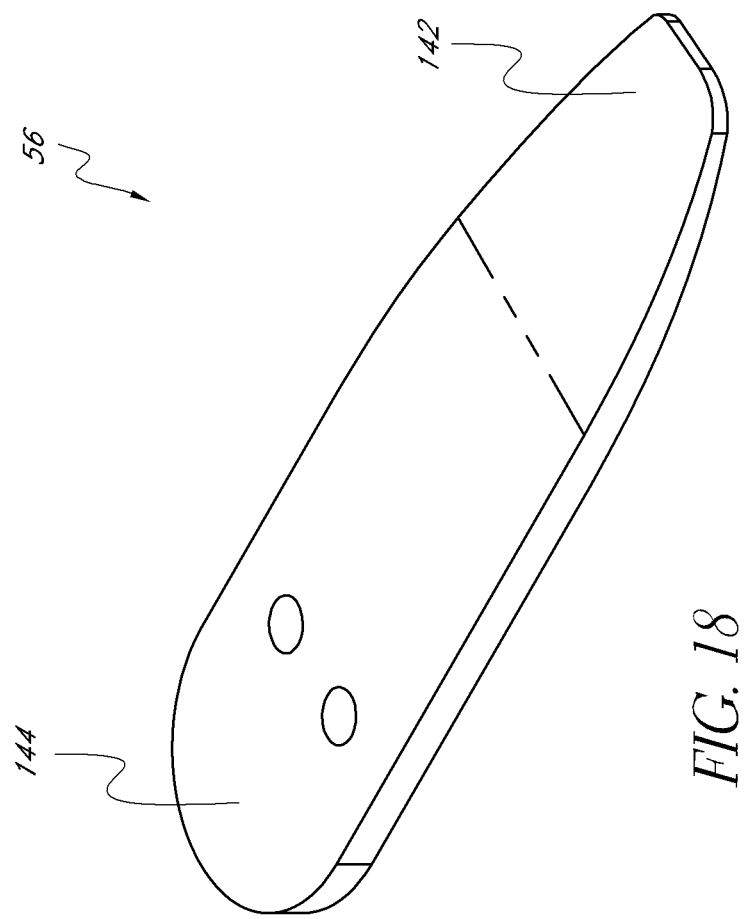

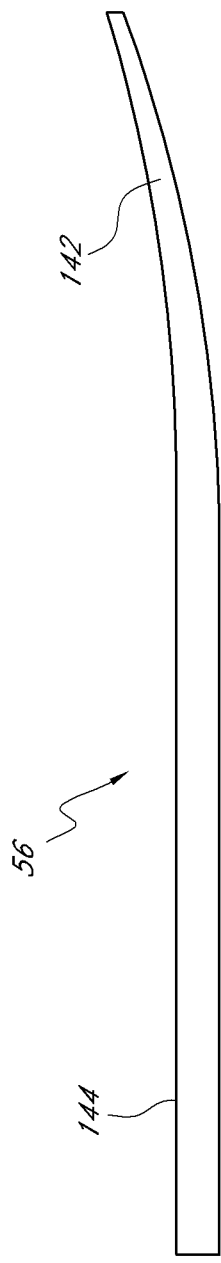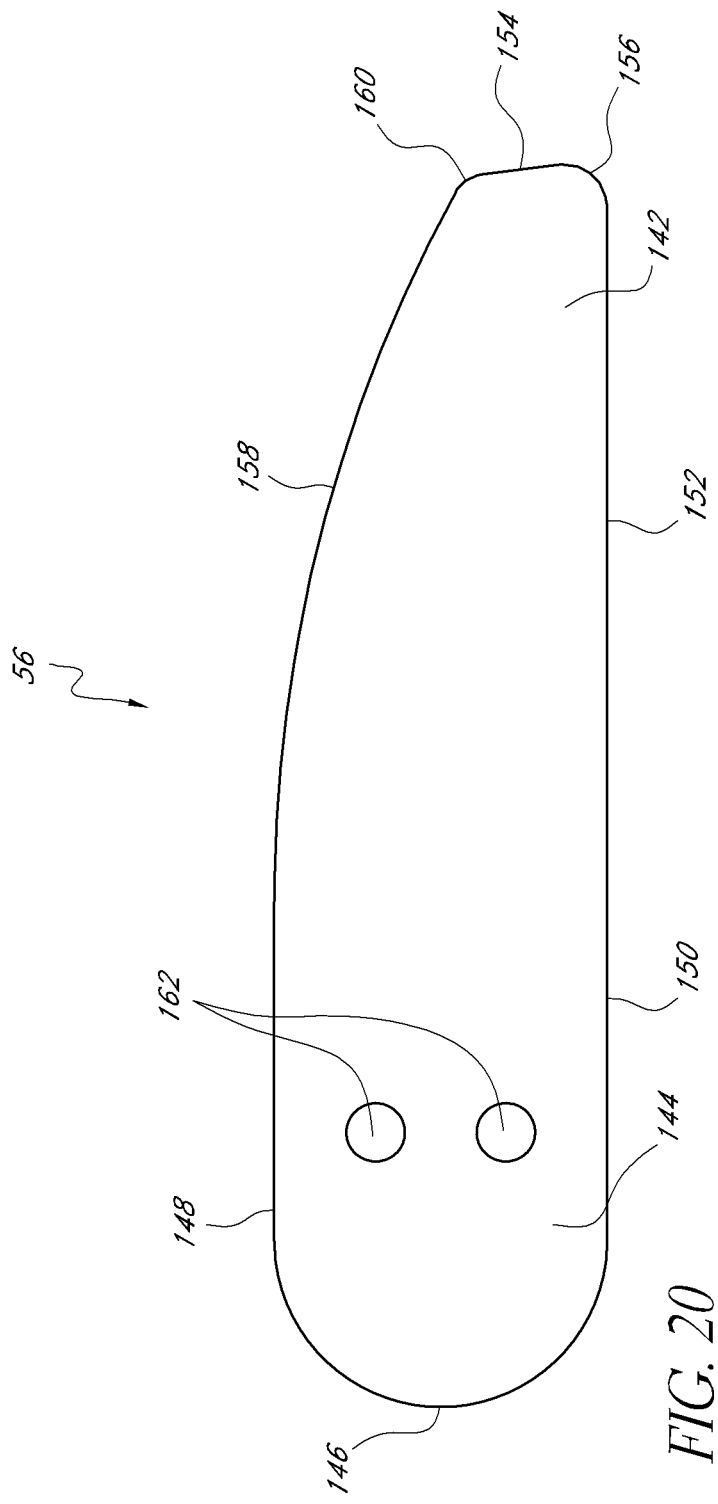

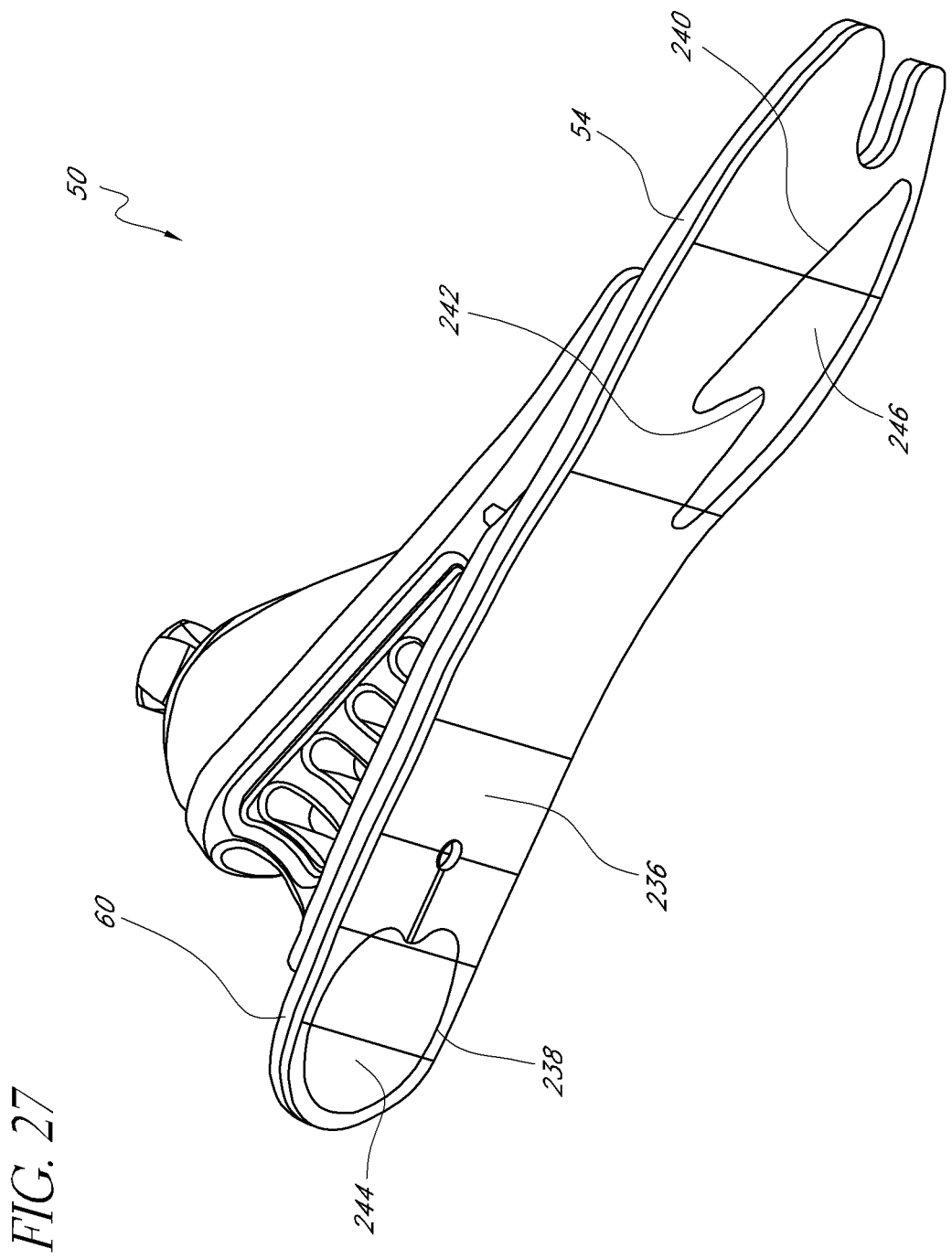

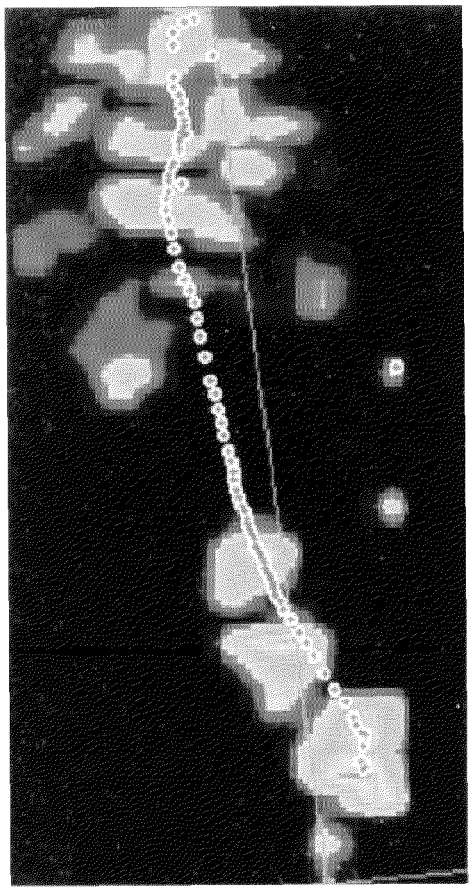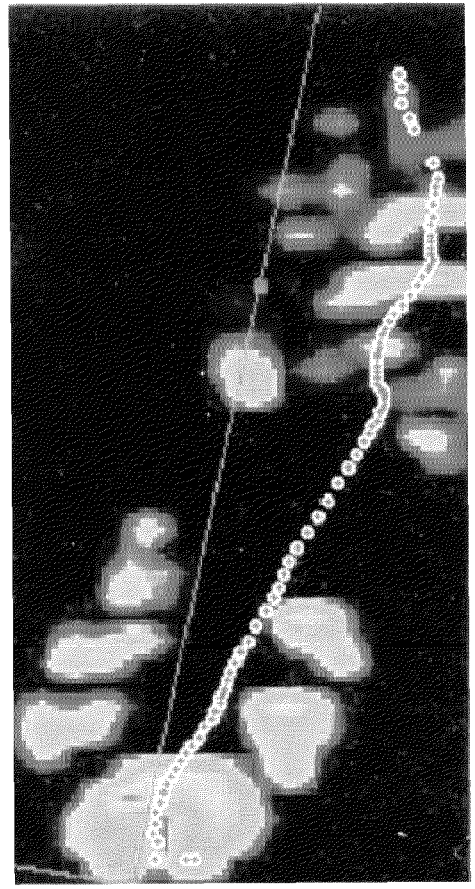
FIG. 41

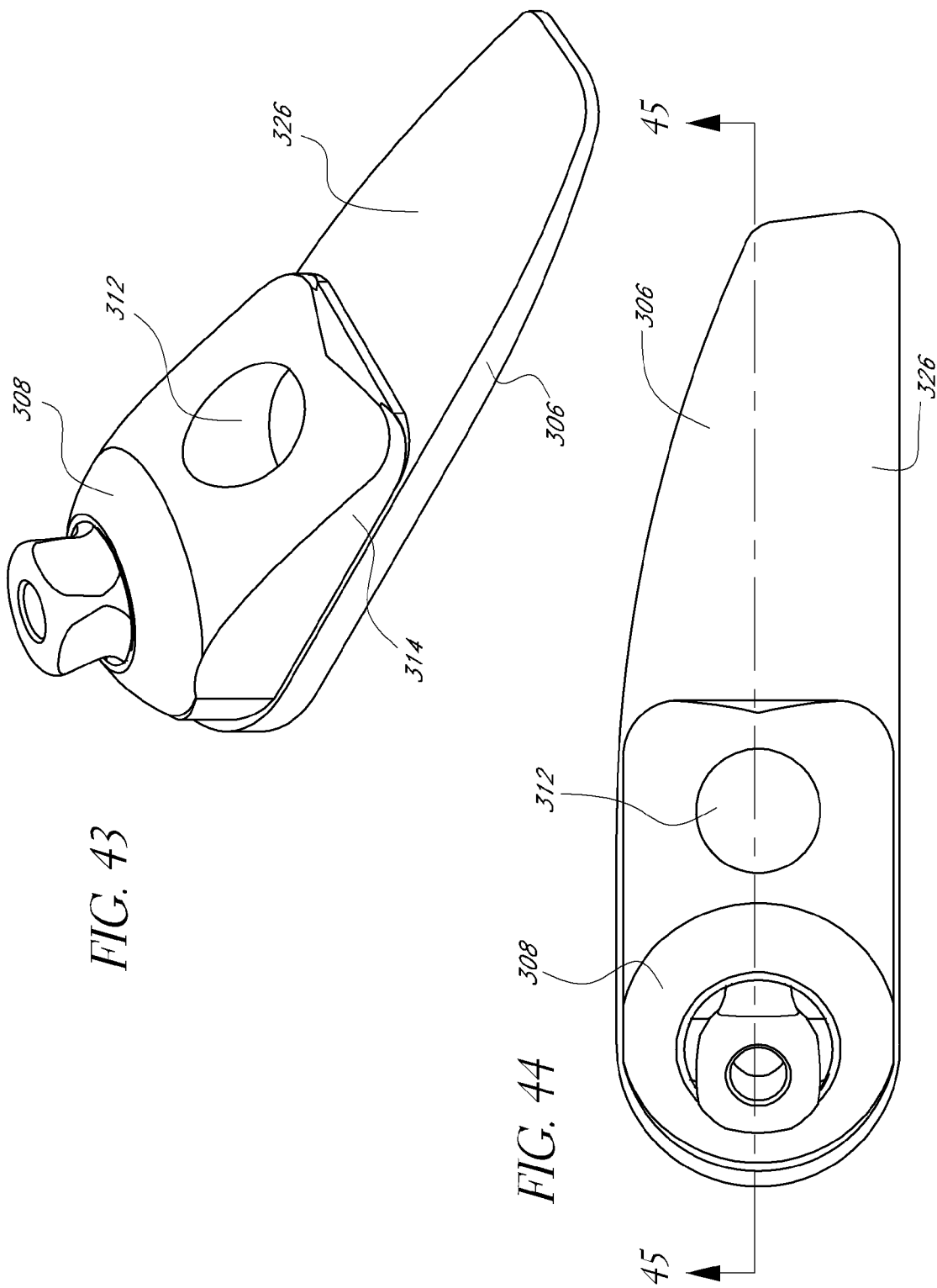

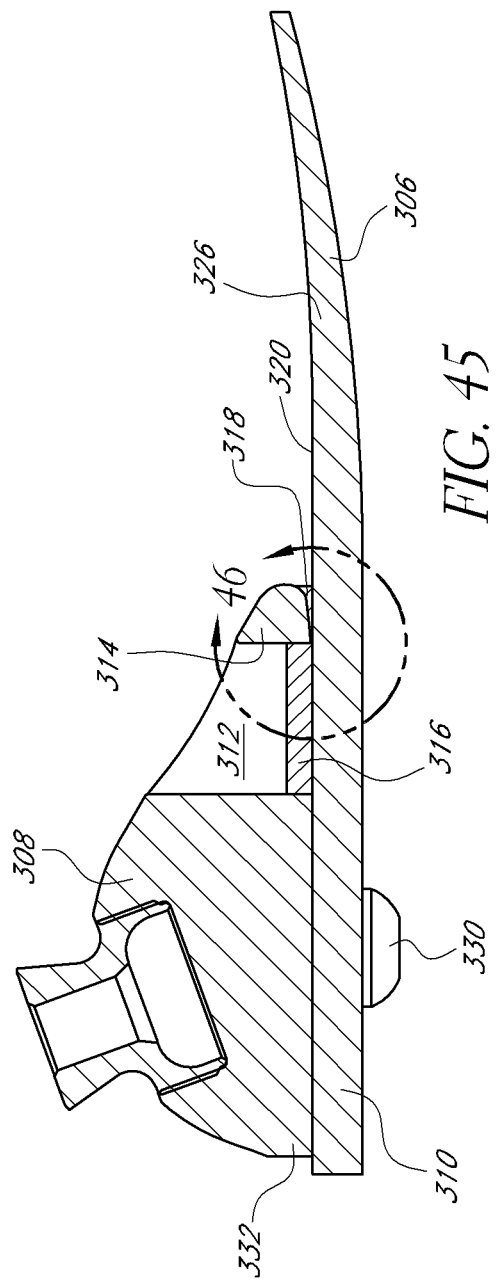
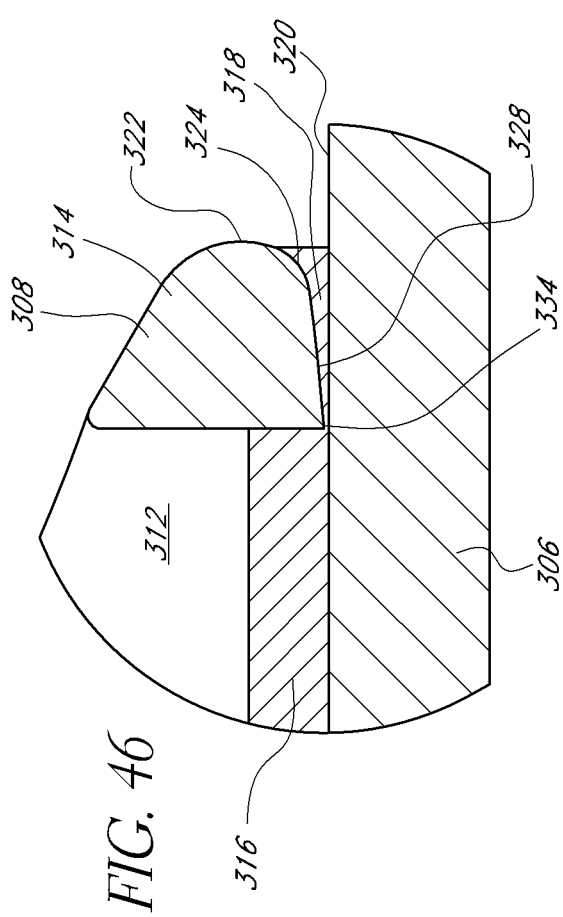

FOOT PROSTHESIS WITH RESILIENT MULTI-AXIAL ANKLE

RELATED APPLICATIONS

This application is a continuation of application Ser. No. 13/196,339, filed Aug. 2, 2011, which is a continuation of application Ser. No. 12/509,010, filed Jul. 24, 2009, now U.S. Pat. No. 7,998,221, which is a continuation of application Ser. No. 10/987,940, filed Nov. 12, 2004, now U.S. Pat. No. 7,846,213, which is a continuation-in-part of application Ser. No. 10/944,436, filed Sep. 17, 2004, now U.S. Pat. No. 7,347,877, which claims priority to provisional application Ser. No. 60/575,142, filed on May 28, 2004. The entire contents of each of these applications are hereby expressly incorporated by reference.

BACKGROUND OF THE INVENTION

Field of the Invention

The present invention relates in certain embodiments to prosthetic feet.

Description of the Related Art

U.S. Pat. Nos. 5,728,177 and 5,800,569 each disclose prosthetic feet having resilient ankles. Each foot generally comprises a lower foot plate, an upper, smaller ankle plate and a layer or block of resilient material that connects the foot plate to the ankle plate. Each foot is sized to fit within an outer flexible cosmesis.

U.S. Pat. Nos. 6,206,934 and 6,280,479 each disclose prosthetic feet having resilient ankle blocks with one or more spring inserts. In each foot, the ankle block is sandwiched between a foot element and an ankle element. The spring inserts increase the rigidity of the foot and alter the energy storage and return characteristics thereof.

SUMMARY OF THE INVENTION

The preferred embodiments of the present foot prosthesis with resilient multi-axial ankle have several features, no single one of which is solely responsible for their desirable attributes. Without limiting the scope of this foot prosthesis as expressed by the claims that follow, its more prominent features will now be discussed briefly. After considering this discussion, and particularly after reading the section entitled "Detailed Description of the Preferred Embodiments," one will understand how the features of the preferred embodiments provide advantages, which include soft heel, stabilization at heel strike, progressive stiffness at heel strike and toe off, smooth rollover, guided rollover, progressively increasing support from mid stance through toe off, natural-feeling toe off, variable stiffness during rollover and a reduction in stresses in members that secure various foot components to one another.

One embodiment of the present foot prosthesis comprises a lower element, an upper element, a resilient ankle member and an attachment adapter operatively connected to an upper surface of the upper element. The ankle member is positioned between the lower and upper elements, and completely separates the lower element from the upper element such that the lower element does not contact the upper element. A gap exists between a lower front edge of the adapter and the upper surface of the upper element.

Another embodiment of the present foot prosthesis comprises, in combination, an elongate, plate-like element adapted for use in a prosthetic foot and an attachment adapter operatively connected to an upper surface of the elongate, plate-like element. A gap exists between a lower front edge of the adapter and the upper surface. The gap contains a resilient material.

Another embodiment of the present foot prosthesis comprises, a method of constructing a prosthetic foot. The method comprises the steps of operatively connecting an attachment adapter to an upper surface of an upper element, such that a gap remains between a lower front edge of the adapter and the upper surface, and filling at least a portion of the gap with a resilient material.

BRIEF DESCRIPTION OF THE DRAWINGS

The preferred embodiments of the present foot prosthesis with resilient multi-axial ankle, illustrating its features, will now be discussed in detail. These embodiments depict the novel and non-obvious foot prosthesis shown in the accompanying drawings, which are for illustrative purposes only. These drawings include the following figures, in which like numerals indicate like parts:

FIG. 8 is a rear perspective view of the resilient ankle member of the foot prosthesis of FIG. 1;

FIG. 9 is a right side elevational view of the resilient ankle member of FIG. 8;

FIG. 10 is a top plan view of the resilient ankle member of FIG. 8;

FIG. 11 is a rear elevational view of the resilient ankle member of FIG. 8;

FIG. 12 is a front perspective view of a preferred embodiment of a stiffening insert for use with the foot prosthesis of FIG. 1;

FIG. 13 is a front elevational view of the stiffening insert of FIG. 12;

FIG. 14 is a left side elevational view of the stiffening insert of FIG. 12;

FIG. 15 is a front perspective view of another preferred embodiment of a stiffening insert for use with the foot prosthesis of FIG. 1;

FIG. 16 is a front elevational view of the stiffening insert of FIG. 15;

FIG. 17 is a left side elevational view of the stiffening insert of FIG. 15;

FIG. 18 is a front perspective view of the upper element of the foot prosthesis of FIG. 1;

FIG. 19 is a left side elevational view of the upper element of FIG. 18;

FIG. 20 is a top plan view of the upper element of FIG. 18;

FIG. 27 is a bottom perspective view of the foot prosthesis of FIG. 1, further including a functional sole;

FIG. 41 is a top view of a scan that maps the movement of the center of pressure of the foot prosthesis of FIG. 1 as the prosthesis rolls over from heel strike to toe off;

FIG. 43 is a front perspective view of the upper ankle element, adapter and resilient wedge of the foot prosthesis of FIG. 42;

FIG. 44 is an upper plan view of the components of FIG. 43;

FIG. 45 is a right side sectional view of the components of FIG. 43, taken along the line 45-45 in FIG. 44; and FIG. 46 is a detail view of the resilient wedge portion of FIG. 45, taken along the line 46.

DETAILED DESCRIPTION OF THE PREFERRED EMBODIMENTS

Figure 1:
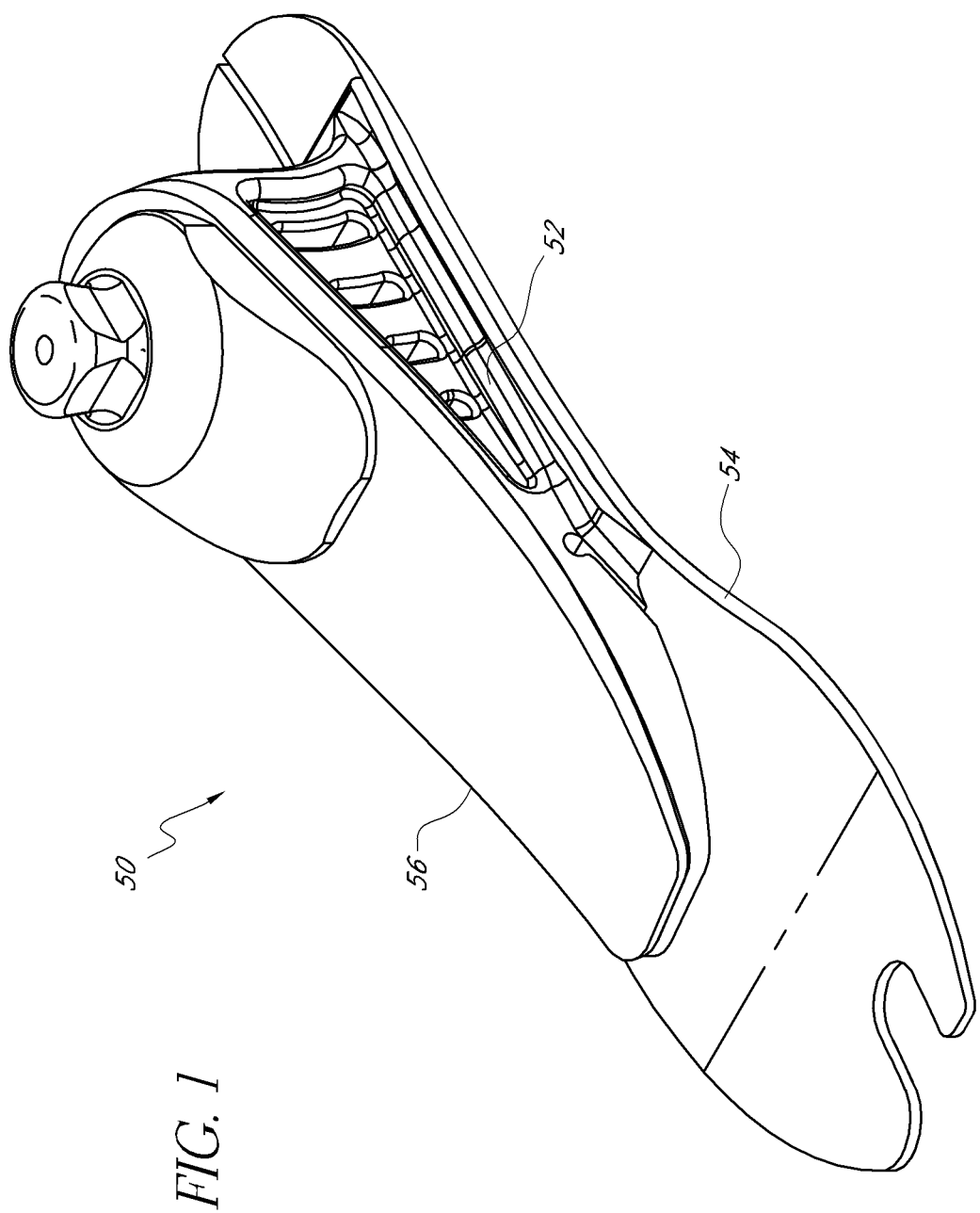
FIG. 1 is a front perspective view of a preferred embodiment of the present foot prosthesis with resilient multi-axial ankle.

FIGS. 1-4 illustrate one embodiment of the present foot prosthesis with resilient ankle. The prosthesis 50 comprises a resilient ankle member 52 sandwiched between a lower element 54, or foot element 54, and an upper element 56 or ankle element 56. In the illustrated embodiment, the foot element 54 and ankle element 56 are substantially plate-like. Those of skill in the art will appreciate, however, that the foot element 54 and ankle element 56 need not resemble plates.

The resilient ankle member 52 sandwiched between relatively stiffer elements 54, 56 enables the foot 50 to flex in multiple planes. The foot 50 is thus able to closely mimic the multiaxial movement capabilities of a natural human foot. Additional applications describe the features and advantages of a resilient ankle member sandwiched between relatively stiffer elements. For example, pending U.S. Patent Publication No. 2003-0093158 A1 discloses a foot prosthesis with a cushioned ankle. Additionally, U.S. Pat. No. 5,800,569 discloses a prosthesis with resilient ankle block.

In one embodiment, the ankle member 52 is constructed of a compressible, resilient and durable material. For example, the ankle member 52 may be constructed of polyurethane. Alternatively, the ankle member may be constructed of foam. The ankle member 52 may be constructed with different shore densities in order to accommodate wearers of different weights. For example, shore densities from 60 A to 90 A could be provided.

In one embodiment, the elements 54, 56 are constructed of a resilient material that is capable of flexing in multiple directions. The material may comprise multiple layers, or laminae. Examples of possible materials for the elements 54, 56 are carbon, any polymer material, and any composite of polymer and fiber. The polymer could be thermoset or thermoplastic. In a composite, the fiber reinforcement could be any type of fiber, such as carbon, glass or aramid. The fibers could be long and unidirectional, or they could be chopped and randomly oriented.

If the elements 54, 56 comprise multiple layers, or laminae, the layers may be arranged as follows. An upper layer and a lower layer may each comprise cloth having fibers oriented at −45° and 45° to a longitudinal axis of the element 54, 56. A next uppermost layer and a next lowermost layer may each comprise a sheet of fibrous material, such as carbon. The fibers may be unidirectional and oriented at 90° to the longitudinal axis. Additional layers in between may each comprise a sheet of fibrous material, such as carbon. The fibers may be unidirectional and oriented within the range of plus or minus 45° to the longitudinal axis. There may be any number of these intermediate layers.

The construction described above provides the elements 54, 56 with multidirectional strength. Additionally, orienting all intermediate layers within the range of plus or minus 45° to the longitudinal axis maximizes fiber surface alignment, which increases the bonding strength between the layers.

In an alternate construction, each of the elements 54, 56 is laid up substantially as described above. However, in the lower element 54, an uppermost layer thereof is oriented within the range of plus or minus 45° to the longitudinal axis, and the element 54 includes no cloth layer on top. Rather, when the element 54 is laid up, a rough weave fabric is placed over the uppermost layer. Prior to curing, this fabric layer is removed. The rough weave leaves behind a roughened surface on the uppermost layer of the element 54. The element 54 is then cured to solidify the roughened upper surface. The lowermost layer of the lower element 54 may be oriented within the range of plus or minus 45° to the longitudinal axis.

In this same construction, the upper element 56 is similarly laid up such that a lowermost layer thereof is oriented within the range of plus or minus 45° to the longitudinal axis, and the element 54 includes no cloth layer on the bottom. The surface of the lowermost layer thereof is roughened in the same manner described above. The roughened surfaces of the elements 54, 56 are adapted to be secured to the respective abutting surfaces of the ankle member 52, as described below. In this construction, the resilient ankle member 52 enhances the multidirectional strength of the elements 54, 56 as it flows over stress areas therein.

This layered construction is illustrated below:
Cloth with fibers at −45° and 45°;
Unidirectional layer at 90°;
A plurality of unidirectional layers within the range of plus or minus 45°;
A lowermost unidirectional layer within the range of plus or minus 45°;
A roughened lower surface;
Ankle member 52;
A roughened upper surface;
An uppermost unidirectional layer within the range of plus or minus 45°;
A plurality of unidirectional layers within the range of plus or minus 45°; and
Cloth with fibers at −45° and 45°.

All layers listed above the ankle member 52 comprise the upper element 56. All layers listed below the ankle member 52 comprise the lower element 54.

In use, the foot 50 may be covered by a cosmesis (not shown) to make the overall assembly appear as natural as possible. For example, Applicant's copending application filed on the same day herewith discloses a functional foot cover that is well adapted for use with the present foot 50. This copending application, titled "Functional Foot Cover", is attached hereto as an appendix and is to be considered a part of this specification, and is expressly incorporated by reference herein in its entirety. Those of skill in the art will appreciate that the foot 50 is fully functional on its own, and may be used without a cosmesis.

Figure 5:
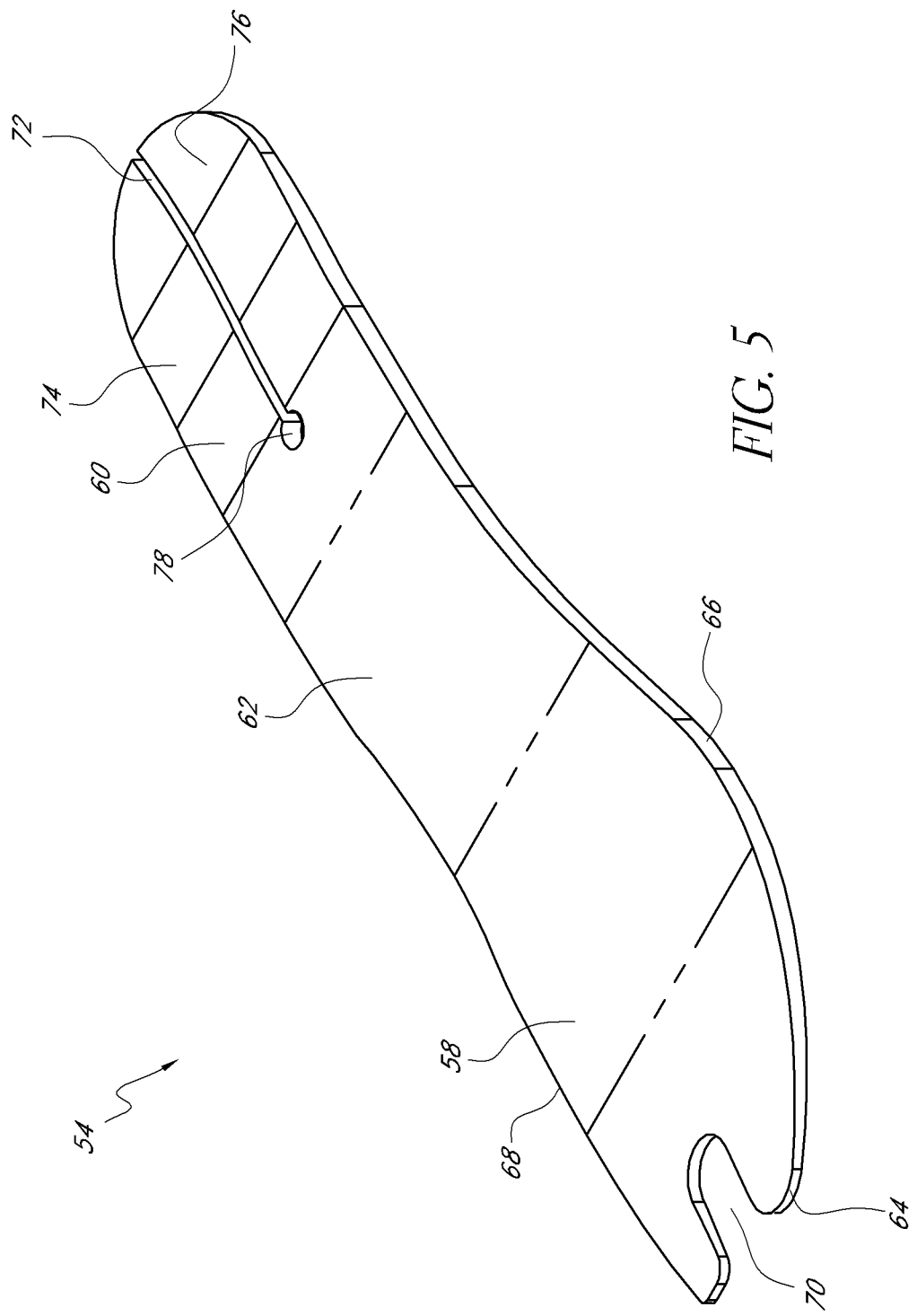
FIG. 5 is a front perspective view of the foot element of the foot prosthesis of FIG. 1.
Figure 6:
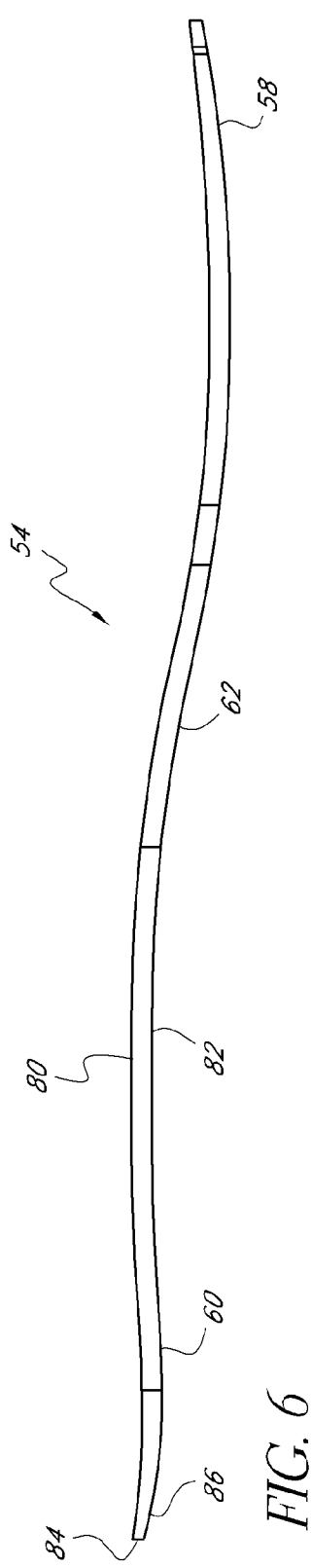
FIG. 6 is a left side elevational view of the foot element of FIG. 5.
Figure 7:
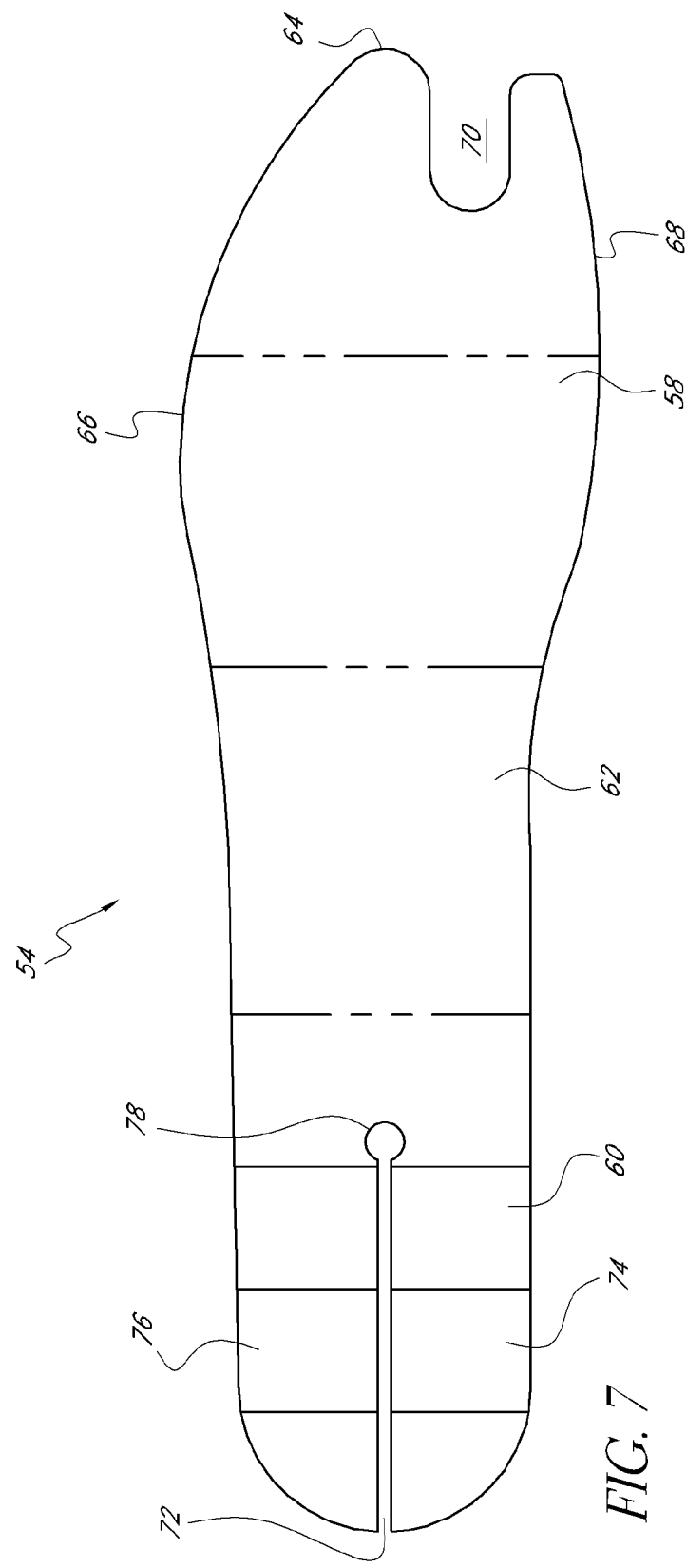
FIG. 7 is a top plan view of the foot element of FIG. 5.
Figure 23:
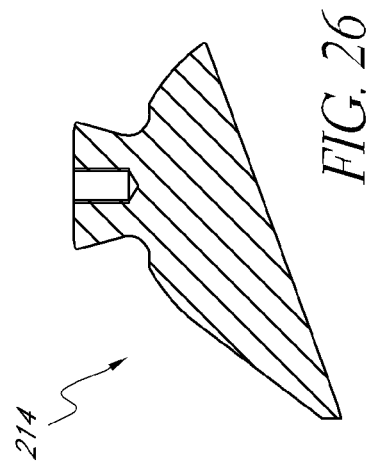
FIG. 23 is a rear elevational view of the adapter of FIG. 21.
Figure 26:
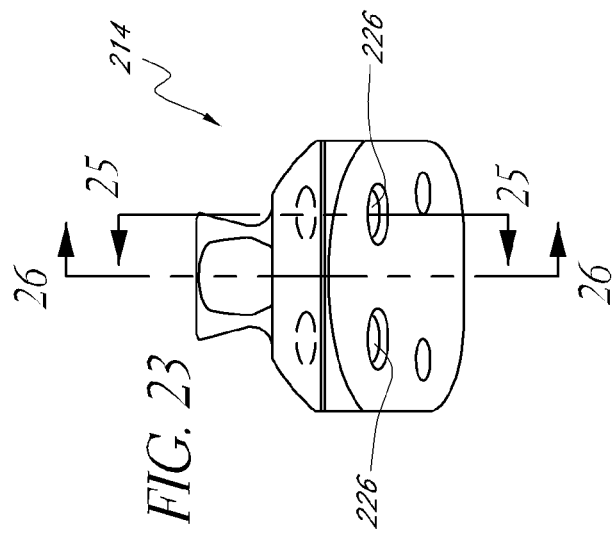
FIG. 26 is a right side sectional view of the adapter of FIG. 21 taken along the line 26-26 in FIG. 23.

With reference to FIGS. 5-7, the foot element 54 includes a toe portion 58, a heel portion 60 and an arch portion 62. The foot element 54 may be sized and shaped similarly to the natural human foot for which it substitutes. Thus, with reference to FIG. 7, the heel portion 60 includes a substantially constant width. The arch portion 62 includes a substantially constant width in a region that is proximate the heel portion 60, and then gradually widens as it approaches the toe portion 58. The toe portion 58 includes a width that increases in a direction away from the arch portion 62, and then tapers inwardly to an anterior edge 64.

The outwardly bulging lateral edge 66 in the toe portion 58 contributes to a more natural toe off. In the human foot, the center of mass travels approximately through the big toe and the second toe as the foot rolls over from heel strike to toe off. In the present foot prosthesis 50, the outwardly curved lateral edge 66 helps to guide the travel of the foot's center of mass toward the medial side 68, so that it travels through the area where the big toe and second toe would be located if a human foot were superimposed over the foot element 54. This path for the center of mass creates a more natural-feeling toe off, which in turn contributes to an overall more natural feel for the wearer of the present prosthesis 50. As described more fully below, the outwardly curved lateral edge 66 does not achieve this advantageous result by itself. Instead, the lateral edge 66 achieves this advantageous result in combination with other features of the foot 50.

The toe portion 58 includes a generally U-shaped cut-out portion 70 at the anterior end 64 thereof. The cut-out 70 is positioned toward a medial side of a longitudinal axis of the foot element 54, but is spaced from the medial edge 68 of the foot element 54. The cut-out 70 gives the foot element 54 a "sandal toe" appearance. This sandal toe is adapted to engage mating structure within a cosmesis. The cosmesis provides the foot 50 with a more anatomical look.

The sandal toe also enables the foot element 54 to maintain a more anatomical look while providing a full length toe lever. The full length toe lever provides greater energy return at toe off and contributes to a full length stride. Further, the cut-out 70 provides the toe portion 58 with a lesser stiffness on the medial side thereof. The lesser stiffness on the medial side enhances the travel of the foot's center of mass toward the medial side as the foot 50 rolls over.

In an alternate configuration (not shown), the cut-out 70 may be positioned toward a lateral side of a longitudinal axis of the foot element 54. In this configuration, the cut-out 70 provides the toe portion 58 with a lesser stiffness on the lateral side thereof. The lesser stiffness on the lateral side enhances the travel of the foot's center of mass toward the lateral side as the foot 50 rolls over.

The heel portion 60 includes a longitudinal split 72 that extends substantially along the longitudinal axis of the foot element 54. The split 72 extends into a region of the arch portion 62 that is proximate the heel portion 60. The split 72 provides a narrow gap between a medial portion 74 and a lateral portion 76 of the heel portion 60. The split 72 terminates in a rounded fillet 78 that helps prevent the formation of stress concentrations in that region. Such stress concentrations could propagate a crack through the foot element 54.

The split 72 in the heel portion 60 helps the heel portion 60 to conform to uneven ground, which helps to stabilize the foot 50 during heel strike. For example, the medial portion 74 may strike a pebble, while the lateral portion 76 strikes flat ground. In such a situation, the separate medial and lateral portions 74, 76 move independently of one another to conform to the uneven ground. The medial portion 74 deflects a greater amount than the lateral portion 76 does. The pebble thus does not place as great a torque on the foot element 54 as it otherwise would in the absence of the heel split 72. Such torque would tend to twist the entire foot 50, leading to overall instability. The heel split 72 helps to avoid such instability.

In one embodiment, illustrated in FIG. 27, a lower surface of the foot element 54 includes a functional sole 234. The sole 234 provides advantageous rollover properties, as described below. The sole 234 is secured, for example by bonding, to the lower surface of the foot element 54. The functional sole 234 comprises portions of resilient and compressible material. Example materials include EVA and polyurethane. In the illustrated embodiment, a first portion 236 of resilient and compressible material covers most of the foot element lower surface. In an alternate embodiment, the first portion 236 may cover the entirety of the foot element lower surface. The first portion 236 includes a perimeter that is shaped substantially the same as the foot element perimeter.

The first portion 236 includes internal irregularly shaped holes. A first hole 238 is substantially round and is located at the heel portion 60. The first hole 238 may be asymmetrically shaped, having first and second projections, one on the medial side of the foot and the other on the lateral side of the foot. The medial projection may extend farther anteriorly than the lateral projection.

A second hole 240 is oblong with a substantially V-shaped indentation 242 and is located approximately where the ball of the foot would be if a human foot were superimposed over the foot element 54. The second hole is preferably provided on the medial side of the foot, with the bottom of the V preferably pointing toward the big toe of the foot.

Inserts 244, 246 comprising resilient and compressible material(s) occupy the holes 238, 240. In one embodiment, the inserts 244, 246 have different material properties than the material comprising the first portion 236. For example, the inserts 244, 246 may be more readily compressible, or less dense, than the first portion material.

The more compressible insert 244 advantageously provides additional shock absorption in the heel portion 60 of the foot 50. Moreover, the asymmetry of the insert 244 toward the medial side, and the medially placed insert 246, provide additional compressibility overall to the medial side of the foot 50. This configuration guides the center of mass of the foot 50 toward the medial side as the foot rolls over from heel to toe. In each of these embodiments, the inserts 244, 246 are preferably surrounded by the material of the first portion 236, to provide desired support to the foot 50 at the edges of the sole 234.

In an alternate configuration, the insert 246 may comprise a material that is less compressible than the material of the first portion 236. In this configuration, the stiffer medial side of the foot 50 guides the center of mass of the foot 50 toward the lateral side as the foot 50 rolls over from heel to toe.

In another alternate configuration, the insert 246 may be located along the lateral side of the toe portion of the foot element 54. In such a configuration, the material composition of the insert 246 affects the rollover properties of the foot 50. If the insert 246 is softer than the first portion 236, then the foot's center of mass is guided toward the lateral side as the foot 50 rolls over from heel to toe. Conversely, if the insert 246 is stiffer than the first portion 236, then the foot's center of mass is guided toward the medial side as the foot 50 rolls over from heel to toe.

Those of skill in the art will appreciate that additional holes could be provided in the first portion 236, and that these additional holes could be positioned anywhere in the first portion 236 to give the foot 50 desired rollover properties. Any additional holes could also be filled with inserts. These additional inserts could have material properties different that are different from one another, and different from the material properties of the first portion 236.

Those of skill in the art will appreciate that although the sole 234 is provided with inserts 244, 246 of different stiffness or compressibility, other techniques may be used to vary the compressibility of the sole 234. For example, small holes or perforations may be provided in desired locations of the sole 234, such as beneath the heel and/or at the ball of the foot on the medial side. The lack of material at these locations can desirably add to the compressibility or reduced stiffness of the sole 234. Any such embodiment that provides a varying stiffness to the sole 234 in desired locations is contemplated. In particular, any embodiment that varies the stiffness of the sole 234 at particular locations to help guide a desired rollover of the foot 50 is contemplated.

With reference to FIG. 6, in one embodiment an upper surface 80 of the foot element 54 includes a concave curvature in the toe portion 58 and the heel portion 60. A lower surface 82 of the foot element 54 includes a concave curvature in the arch portion 62. The upwardly curved heel portion 60 helps to ensure that the heel portion 60 does not strike the ground along the posterior edge 84. Instead, a portion 86 of the heel forward of the posterior edge 84 strikes the ground during heel strike. This portion 86 has a greater surface area than the posterior edge 84. Thus, at heel strike, the foot 50 is more stable because more of it is in contact with the ground.

The upwardly curved toe portion 58 (and the convex curvature on the foot element 54 lower surface at the toe portion 58) provides an easier rollover through the toe portion 58. The curved arch portion 62 simulates the natural curvature of the arch in the human foot. The foot element 54 thus provides a more natural rollover through the mid stance. In addition, the arch portion 62 tends to flex through the mid stance, which provides additional shock absorption.

With continued reference to FIG. 6, in one embodiment the foot element 54 has a variable thickness along its length. The toe and heel portions 58, 60 are relatively thin, while the arch portion 62 is relatively thick. If the material composition of the foot element 54 is uniform over its entire area, then the areas of variable thickness will provide the foot element 54 with areas of variable stiffness. In the configuration shown in FIG. 6, for example, the toe and heel portions 58, 60 are relatively more flexible than the arch portion 62 is. This configuration provides an easier rollover, because the foot element 54 is more compliant at the toe and heel portions 58, 60. Those of skill in the art will appreciate that the foot element 54 need not include areas having different thicknesses or different stiffnesses.

The foot element 54 may include areas having different material composition. Such material variation may lead to areas of the foot element 54 having different stiffnesses. The areas having different stiffness contribute to a beneficial guided rollover, which is described in more detail below. Examples of configurations for foot elements having areas with different material composition are described below.

FIGS. 28-31 and 34-37 illustrate alternative embodiments for the foot element. The foot elements 88, 90, 92 of FIGS. 28-30 each include two blades 94, 96, 98, 100, 102, 104 arranged side-by-side lengthwise. The blades 94, 96, 98, 100, 102, 104 may comprise portions of a unitary foot element including a lengthwise split 106, the split 106 having a gap 108 in the arch portion 110 of the element 88, 90, 92. Alternatively, the blades 94, 96, 98, 100, 102, 104 may comprise separate portions that are joined to one another at the arch portion 110.

The blades 94, 96, 98, 100, 102, 104 may be constructed of the same material, or they may be constructed of different materials. Each blade 94, 96, 98, 100, 102, 104 may have the same thickness, or one blade 94, 96, 98, 100, 102, 104 may be thicker than the other. To guide the foot's center of mass medially, the medial blade 94, 98, 102 may have a lesser stiffness than the lateral blade 96, 100, 104. The medial blade 94, 98, 102 thus bends more easily than the lateral blade 96, 100, 104, guiding the rollover toward the medial side. Conversely, to guide the foot's center of mass laterally, the medial blade 94, 98, 102 may have a greater stiffness than the lateral blade 96, 100, 104.

Figure 28:
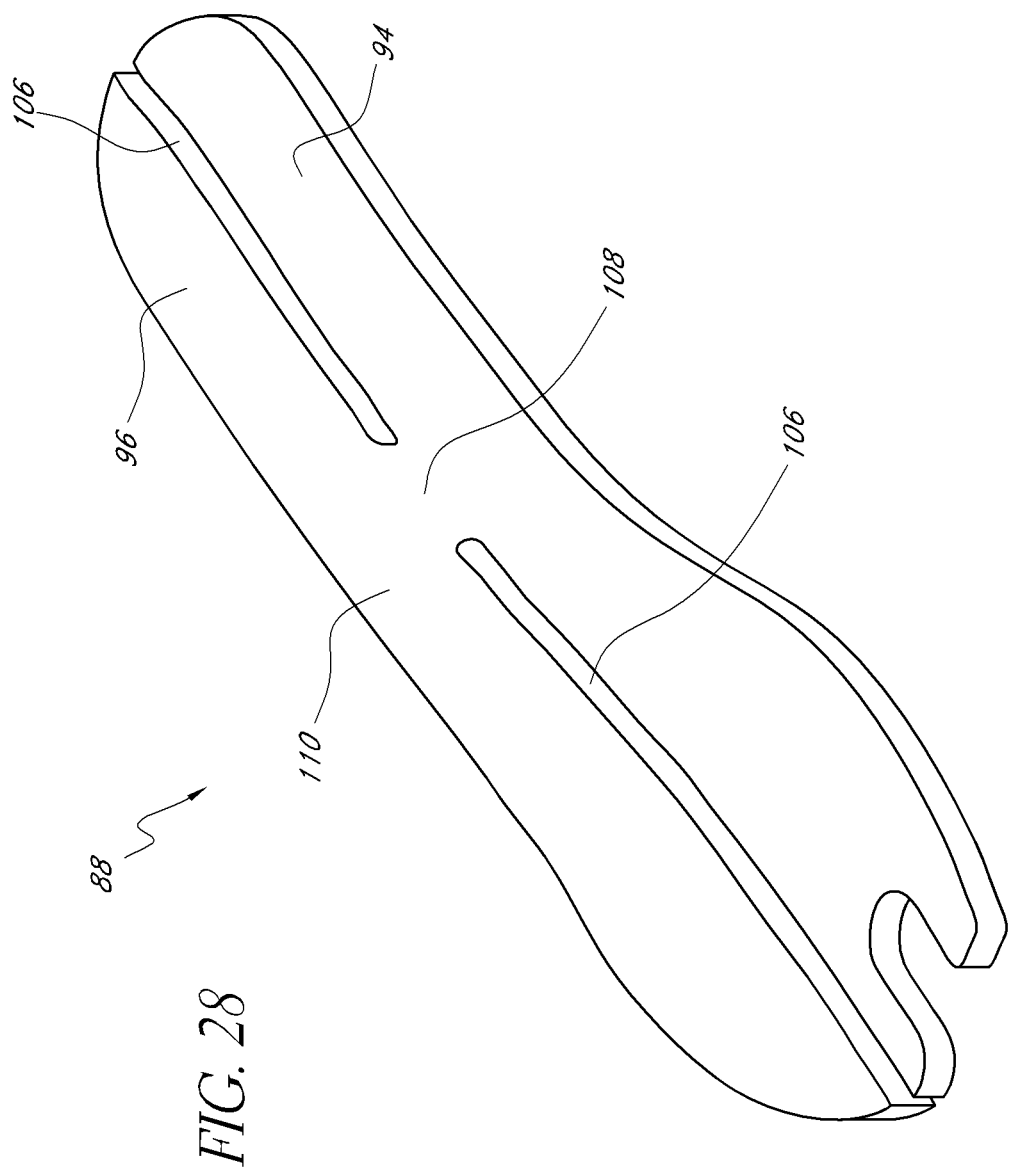
FIG. 28 is a front perspective view of an alternative foot element.
Figure 29:
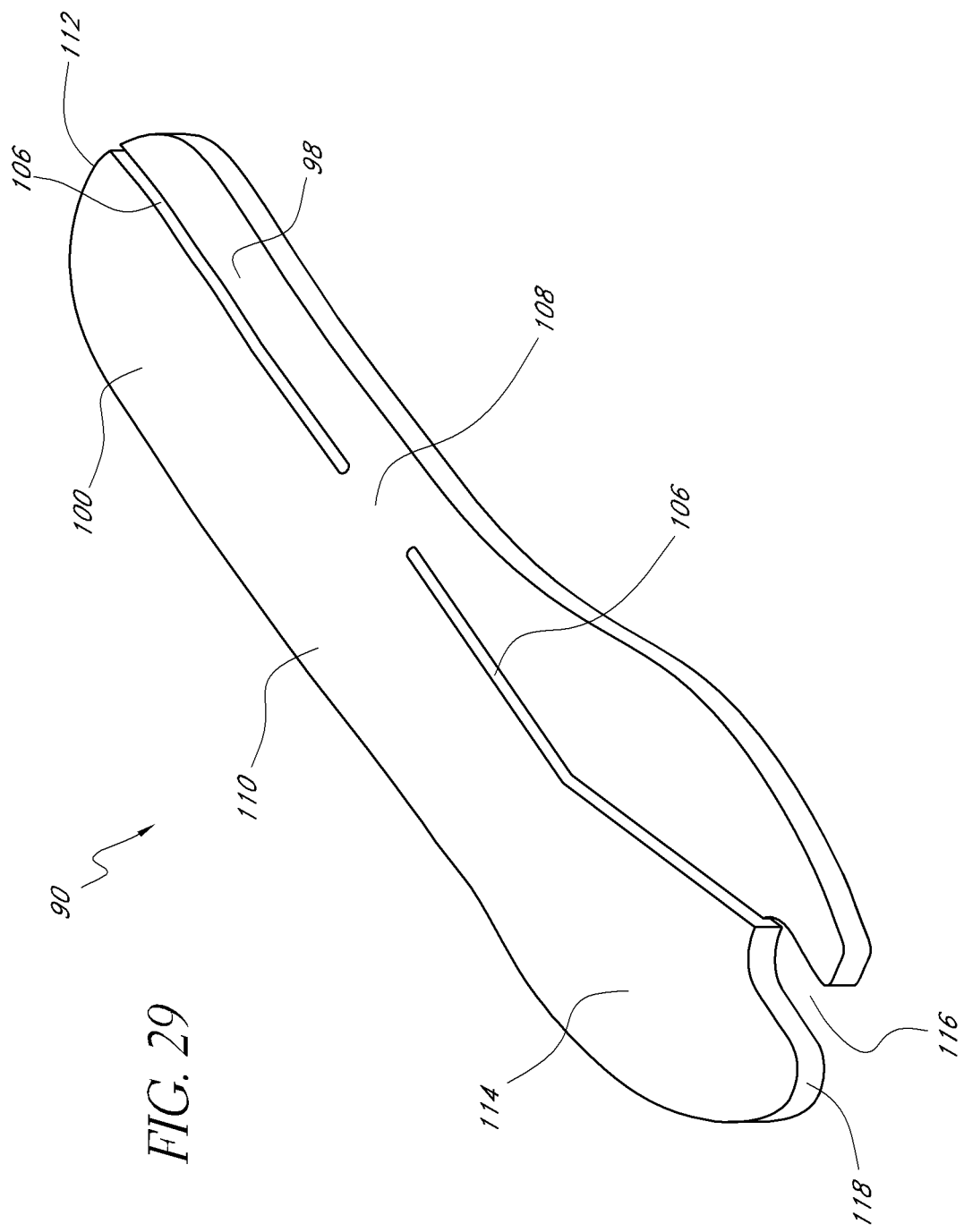
FIG. 29 is a front perspective view of another alternative foot element.
Figure 30:
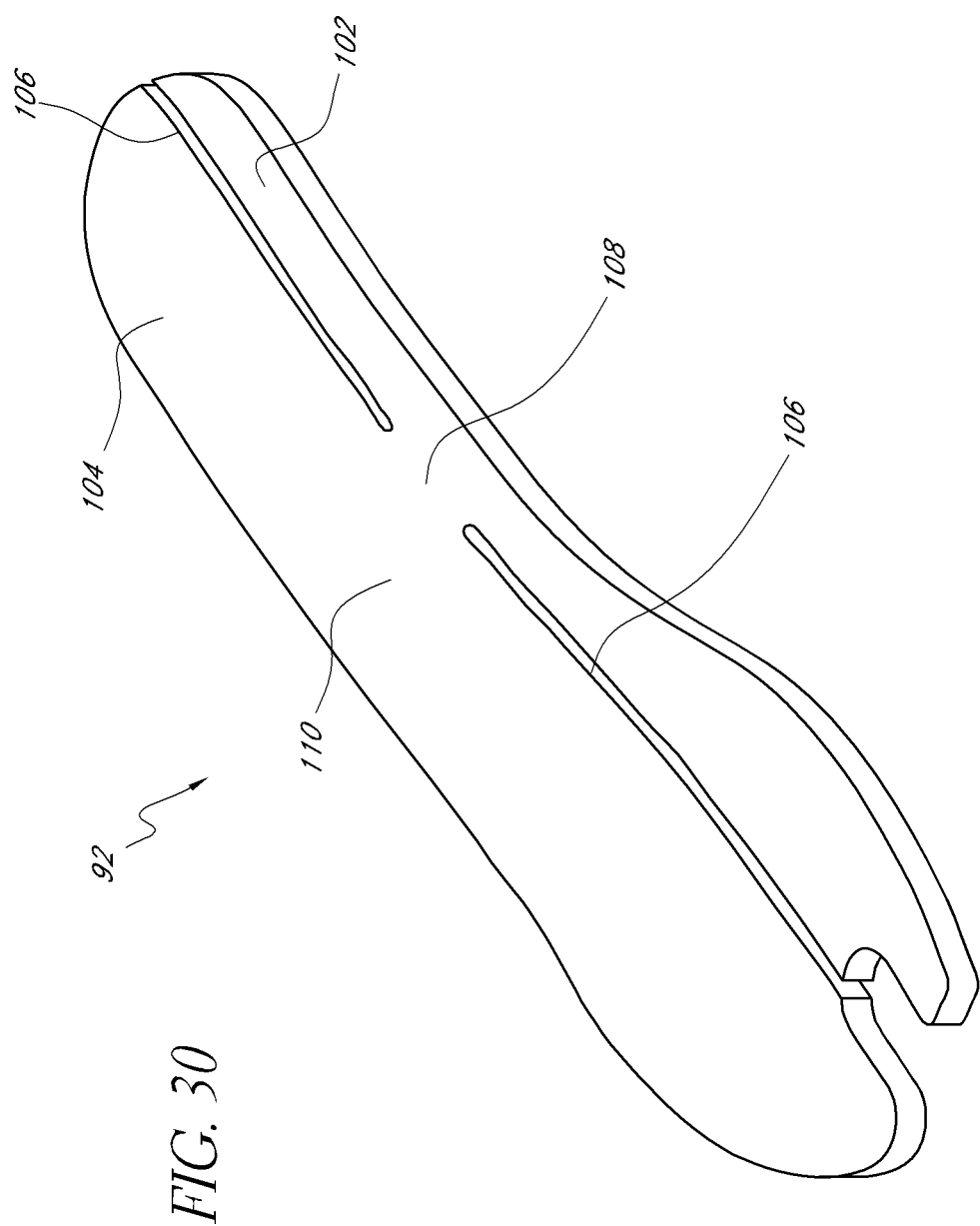
FIG. 30 is a front perspective view of another alternative foot element.

In the embodiment of FIG. 28, the blades 94, 96 have approximately equal widths, and the split 106 runs substantially straight in an anterior/posterior direction. In the embodiment of FIG. 30, the medial blade 102 has a lesser width than the lateral blade 104, and the split runs 106 substantially straight in an anterior/posterior direction. In the embodiment of FIG. 29, the medial blade 98 has a lesser width than the lateral blade 100, and the split 106 includes a change in direction. The split 106 runs substantially straight in an anterior/posterior direction from the posterior edge 112 of the element 90 to the arch portion 110. After a short gap 108, the split 106 continues substantially straight in an anterior/posterior direction until it reaches approximately a border between the arch portion 110 and the toe portion 114. The split 106 then turns medially and continues to the base of the U-shaped cutout 116 in the anterior edge 118 of the toe portion 58.

Figure 31:
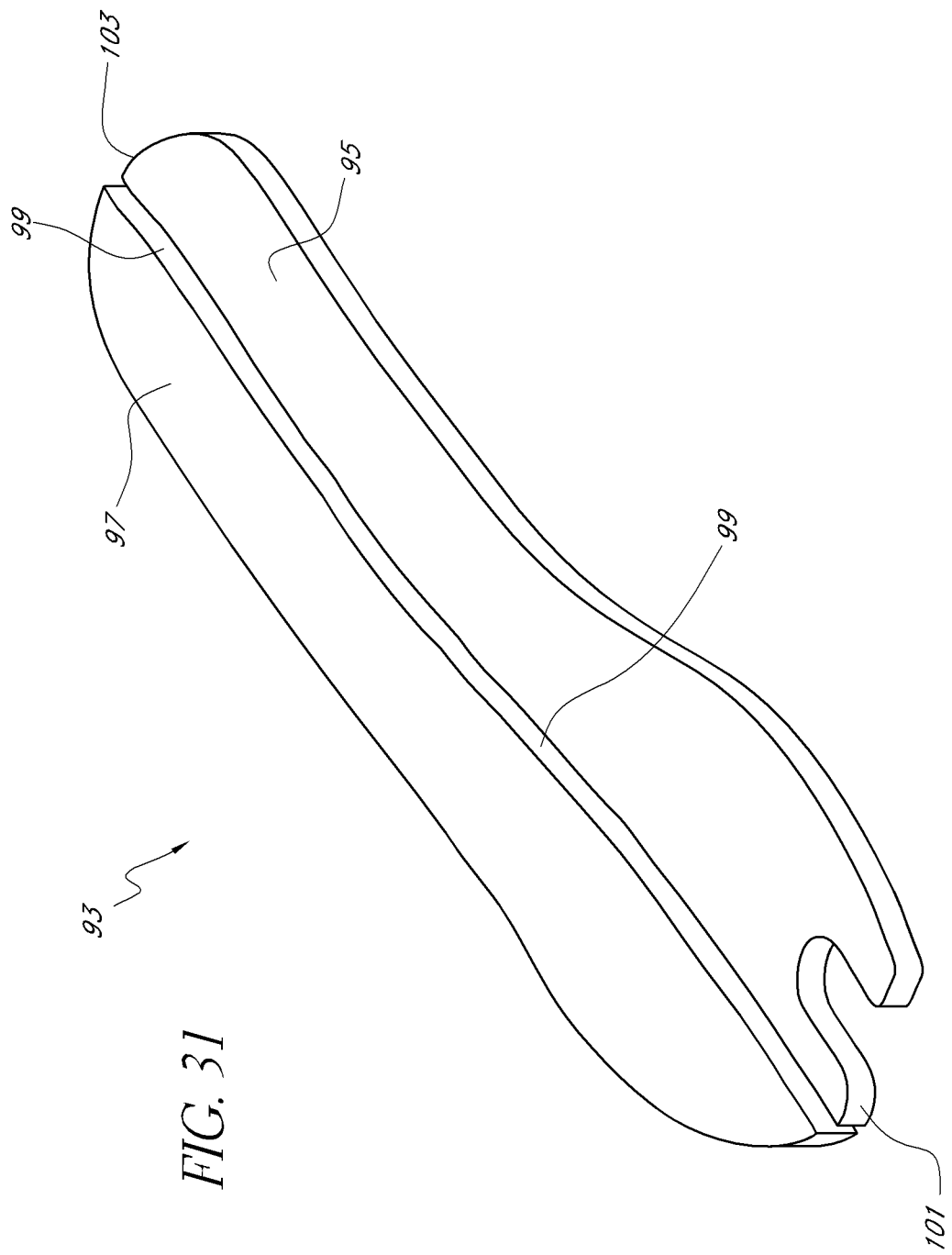
FIG. 31 is a front perspective view of another alternative foot element.

FIG. 31 illustrates another alternative embodiment for the foot element. The foot element 93 of FIG. 31 includes two blades 95, 97 arranged side-by-side lengthwise. The blades 95, 97 may comprise portions of a unitary foot element including a lengthwise split 99 that extends from an anterior edge 101 to a posterior edge 103 thereof. Alternatively, the blades 95, 97 may comprise separate portions.

The blades 95, 97 may be constructed of the same material, or they may be constructed of different materials. Each blade 95, 97 may have the same thickness, or one blade 95, 97 may be thicker than the other. To guide the foot's center of mass medially, the medial blade 95 may have a lesser stiffness than the lateral blade 97. The medial blade 95 thus bends more easily than the lateral blade 97, guiding the rollover toward the medial side. Conversely, to guide the foot's center of mass laterally, the medial blade 95 may have a greater stiffness than the lateral blade 97.

The foot elements 88, 90, 92, 93 described above all include split heel and toe portions. These split portions provide the same advantageous ground compliance described above with respect to the split heel portion 60.

Figure 35:
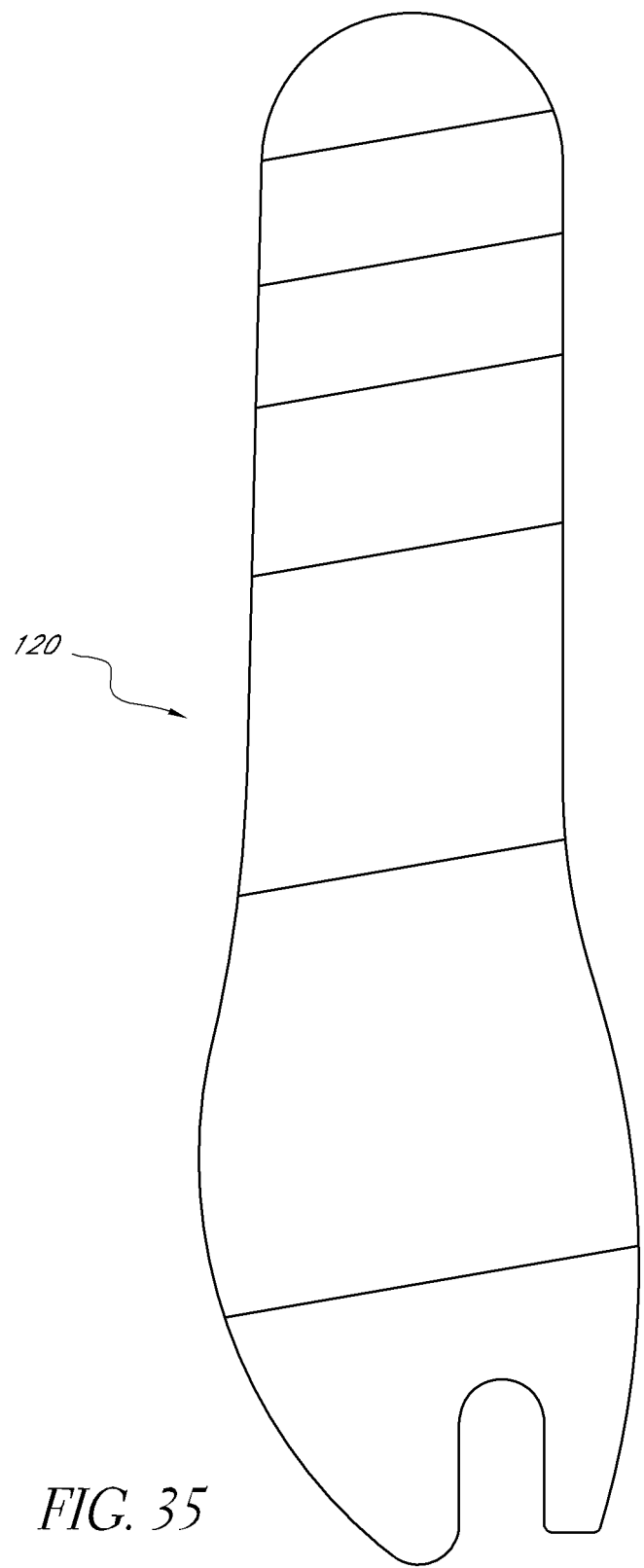
FIG. 35 is a front perspective view of another alternative foot element.

The embodiment of FIG. 35 comprises a unitary foot element 120. The curvature of the blade is angled medially. This angled curvature guides the foot's center of mass medially during rollover. In an alternate configuration, the curvature of the blade may be angled laterally. This angled curvature guides the foot's center of mass laterally during rollover.

Figure 36:
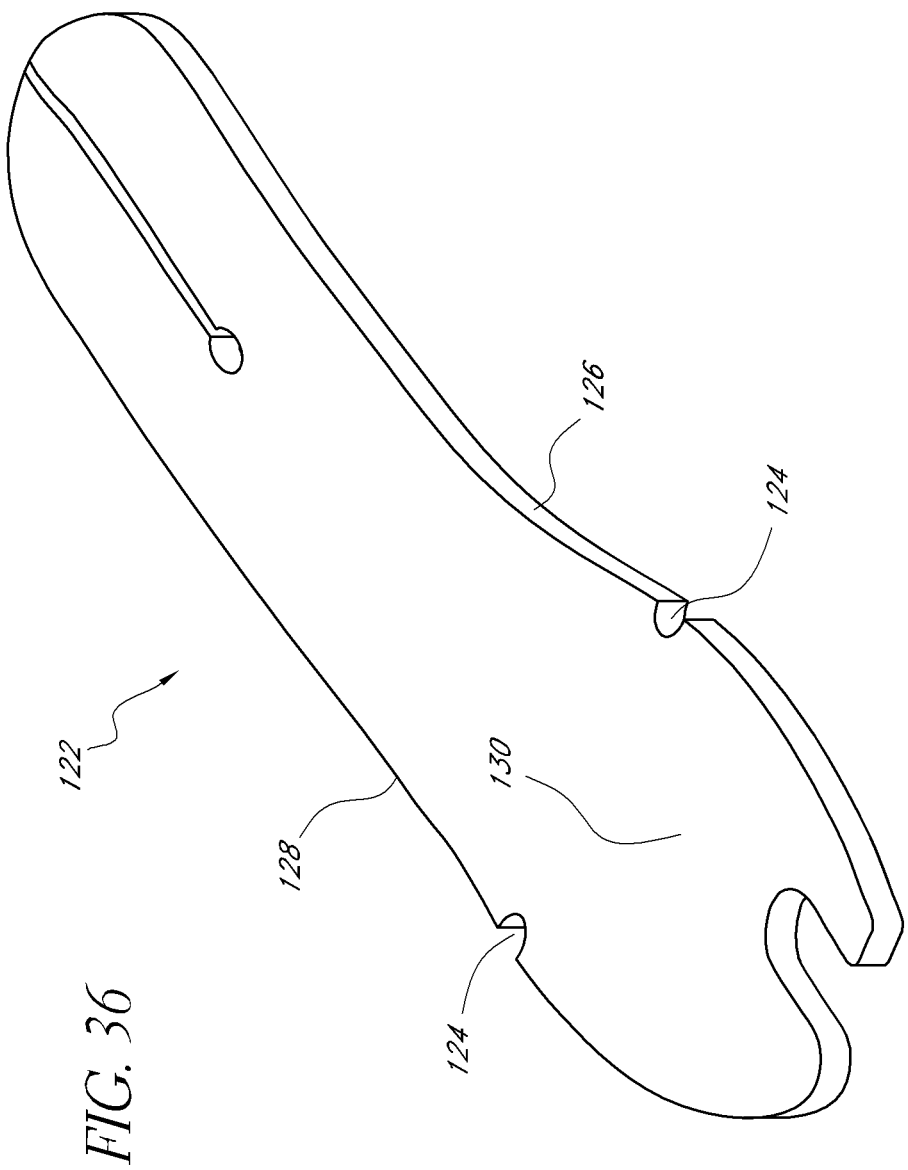
FIG. 36 is a front perspective view of another alternative foot element.

The embodiment of FIG. 36 similarly comprises a unitary foot element 122. Side cuts 124 in the medial edge 126 and lateral edge 128 of the toe portion 130 control the foot element bending angle. In the illustrated embodiment, the side cuts 124 are substantially U-shaped in top plan aspect. Those of skill in the art will appreciate, however, that the side cuts 124 could embody substantially any shape. For example, the side cuts 124 could be V-shaped.

Figure 37:
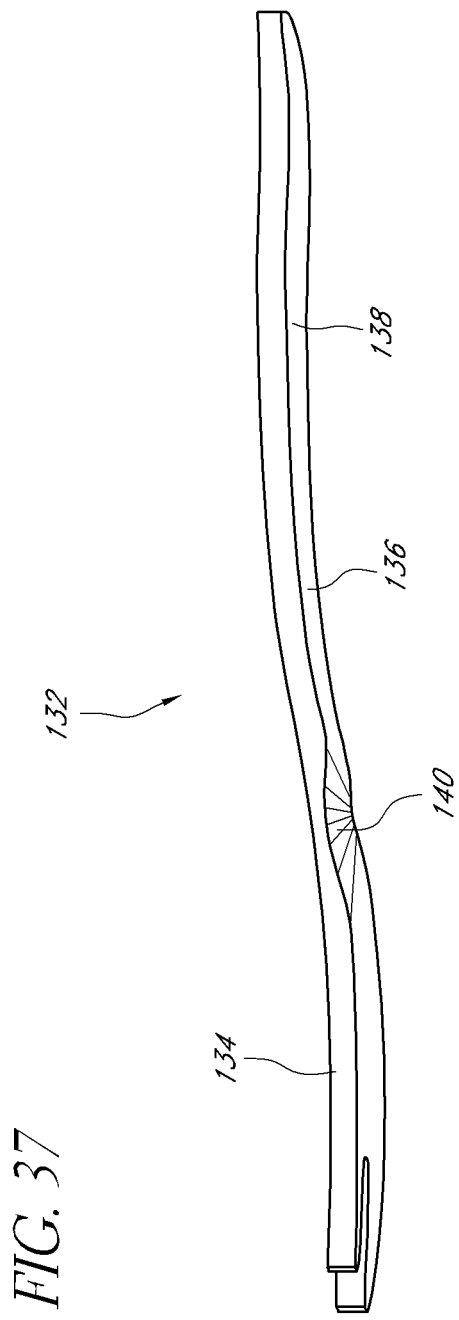
FIG. 37 is a front perspective view of another alternative foot element.

The embodiment of FIG. 37 comprises a unitary foot element 132. At approximately a border between the toe portion 134 and arch portion 136, a lower surface 138 of the element includes a channel 140. The channel 140 runs approximately perpendicular to a longitudinal axis of the element 132. The channel 140 may, however, run in a direction that is not perpendicular to the longitudinal axis of the element 132. For example, a medial end of the channel 140 may lie posterior to a lateral end of the channel 140, and vice versa.

A depth of the channel 140 increases in the medial direction. In the region of the channel 140, the medial side of the element 132 is thus more flexible than the lateral side. This configuration guides the foot's center of mass toward the medial side during rollover. In an alternate configuration, a depth of the channel 140 may increases in the lateral direction. In the region of the channel 140, the lateral side of the element 132 is thus more flexible than the medial side. This configuration guides the foot's center of mass toward the lateral side during rollover.

FIGS. 18-20 illustrate the upper element 56 in detail. With reference to FIG. 18, the upper element 56 includes a front portion 142 and a rear portion 144. Although the rear portion 144 of the upper 56 element is illustrated as being substantially planar, those of skill in the art will appreciate that the rear portion 144 could curve upwardly to form a generally vertical or angled upper attachment section.

With reference to FIG. 20, the rear portion 144 includes a substantially semi-circular posterior edge 146, a substantially straight medial edge 148, and a substantially straight lateral edge 150. Those of skill in the art will appreciate that any of these edges 146, 148, 150 may comprise different shapes. The front portion 142 includes a substantially straight lateral edge 152 that extends forward to a substantially straight anterior edge 154. The anterior edge 154 is slightly angled so that a lateral portion thereof extends forward of a medial portion thereof. An intersection of the lateral edge 152 and the anterior edge 154 defines a rounded corner 156. A medial edge 158 of the front portion 142 tapers laterally toward the anterior edge 154, intersecting the anterior edge 154 in another rounded corner 160. This asymmetrical shape of the upper element 56 provides the foot 50 with advantageous rollover properties, as described in detail below.

The anterior edge 154 is preferably perpendicular to an axis defined by the forward walking motion of the wearer. To achieve this configuration, the anterior edge 154 preferably intersects a longitudinal axis of the upper element 56 at an angle between about 3 and 20 degrees, more preferably about 7 degrees. For most prosthetic foot devices, to mimic a natural human foot, the prosthetic foot is attached such that its longitudinal axis, defined posterior to anterior, is offset by about 3 to 20 degrees, more preferably by about 7 degrees, toward the lateral side, from an axis defined by the forward walking motion of the wearer. Thus, when the present foot 50 is offset in this manner, the angled anterior edge 154 of the upper element 56 is substantially perpendicular to the axis defined by the forward walking motion of the wearer. This configuration allows for a more evenly distributed bending of the upper element 56 across the anterior edge 154.

With reference to FIG. 19, the rear portion 144 of the upper element 56 is substantially flat, while the front portion 142 curves upwardly. This curvature, in combination with the unique shape of the anterior portion of the ankle member 52, provides the foot 50 with advantageous rollover properties, as described in detail below.

With reference to FIG. 20, the rear portion 144 includes first and second holes 162. The holes 162 are arranged along a line that intersects the longitudinal axis of the element 56 substantially perpendicularly. The holes 162 are substantially equidistant from the longitudinal axis. The holes 162 allow fastening members to protrude upwardly through the upper element 56, as described below.

FIGS. 8-11 illustrate the resilient ankle member 52 in detail. With reference to FIG. 9, the ankle member 52 is substantially wedge shaped in side elevational aspect. An upper surface 164 of the ankle member 52 is substantially flat, but curves upwardly slightly toward an anterior edge 166 thereof. Because the ankle member 52 upper surface 164 is substantially flat, the upper element 54 is also preferably substantially flat at least along a majority of the ankle member 52. The upper element 54 desirably extends upwardly along this flat portion at an angle of between about 10 and 30 degrees from horizontal, more preferably about 20 degrees from horizontal, when the foot 50 is at rest.

Figure 4:
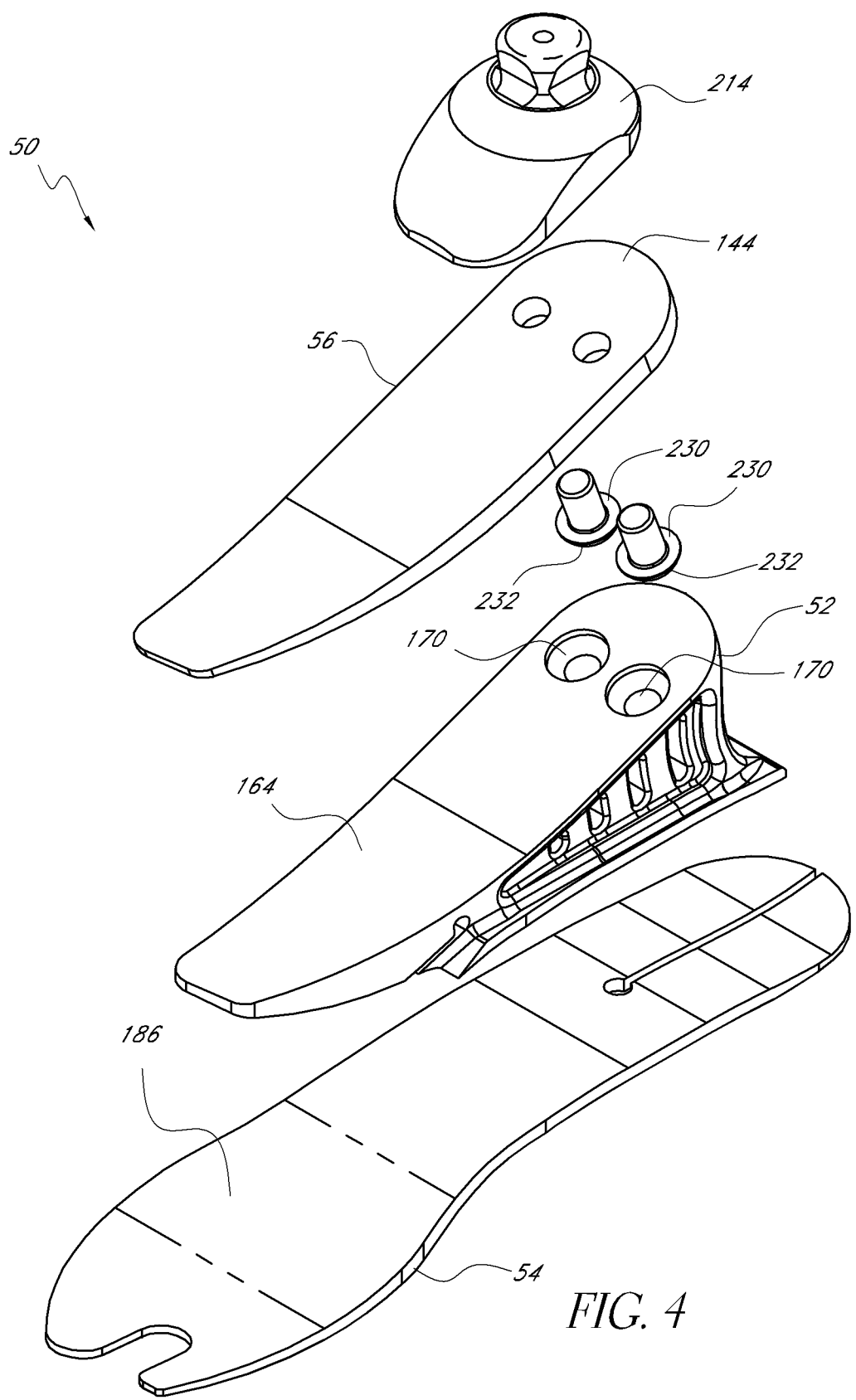
FIG. 4 is an exploded assembly view of the foot prosthesis of FIG. 1, illustrating the prosthesis from a front perspective view.

With reference to FIGS. 8 and 10, a rear portion 168 of the upper surface 164 includes first and second indentations 170. The indentations 170 are arranged along a line that is substantially perpendicular to a longitudinal axis of the ankle member 52. In the assembled foot 50, the indentations 170 receive heads of fastening members, as shown in FIG. 4.

In side elevational aspect (FIG. 9), a rear surface 172 of the ankle member 52 includes a concave curvature of substantially constant radius. Those of skill in the art will appreciate that the curvature need not have a substantially constant radius. The curved rear surface 172, combined with other features of the ankle member 52, creates advantageous results at heel strike, as described in detail below.

Figure 2:
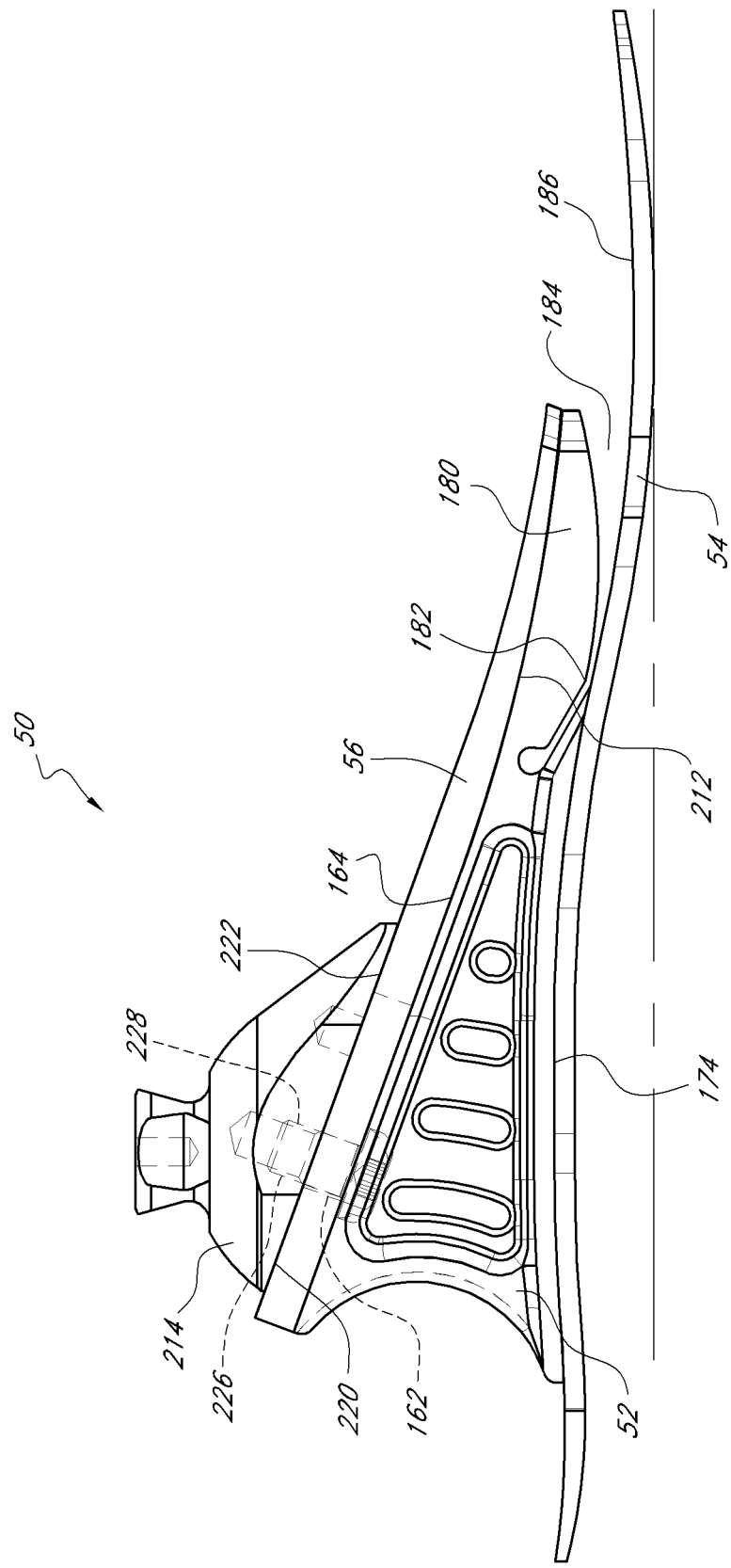
FIG. 2 is a left side elevational view of the foot prosthesis of FIG. 1.

A lower surface 174 of the ankle member 52 includes a concave curvature in a rear portion 176 and an intermediate portion 178 thereof, and a convex curvature in a front portion 180 thereof. With reference to FIG. 2, a narrow gap 182 separates the anterior portion 180 of the ankle member 52 from the foot element 54 when the foot 50 is at rest. The gap 182 may have virtually any size, and may actually be nonexistent. That is, the anterior portion 180 of the ankle member 52 may contact the foot element 54 at 182. Preferably, however, the gap is between 1 mm and 15 mm.

Forward of the gap 182, the upward curvature of the ankle member anterior portion 180 creates a progressively wider wedge-shaped gap 184 between the anterior portion 180 and the upper surface 186 of the foot element 54. The gap 184 creates advantageous rollover properties, as described in detail below.

With reference to FIGS. 8 and 9, side surfaces of the ankle member 52 include substantially wedge-shaped shallow depressions 188 in rear portions thereof. Each depression 188 includes a border 189 that defines a closed shape and separates the areas of differing elevation on the side surfaces.

Within the depressions 188, the side surfaces include a plurality of slots 190. Each slot 190 extends into the ankle member 52 in a direction substantially perpendicular to a longitudinal axis of the ankle member 52. However, the slots 190 preferably do not extend entirely through the ankle member 52. Instead, a longitudinally extending wall (not shown) divides the slots 190 on the medial side from those on the lateral side. This wall may be formed integrally with the ankle member 52. Those of skill in the art will appreciate that the slots 190 could extend entirely through the ankle member 52. In the illustrated embodiment, the ankle member 52 includes four slots 190. However, those of skill in the art will appreciate that fewer or more slots 190 could be provided.

The slots 190 are substantially oval or kidney-shaped in side elevational aspect, transitioning from taller to shorter in an anterior direction. Preferably, one or more of the slots 190 has a kidney shape. For example, the two slots 190 located most posteriorly include curved side edges 192 (FIG. 9), with all of these side edges 192 being concave toward the posterior surface 172 of the ankle member 52. This shape allows more desired buckling of the ankle member 52 toward its posterior portion under load. The posterior portion of the ankle member 52 thus provides additional compression and/or shock absorption, and progressive dampening, as described below. Those of skill in the art will appreciate that the ovals and/or kidneys may stand substantially straight, or they may be tilted. Those of skill in the art will further appreciate that the curved side edges 192 may face toward the anterior edge 166 of the ankle member 52.

The slots 190 are adapted to receive stiffening members, such as those shown in FIGS. 12-17. FIGS. 12-14 illustrate stiffening members 194 having a curved configuration that is adapted to fit into the curved slots 190 (two aftmost slots). FIGS. 15-17 illustrate stiffening members 196 having a straight configuration that is adapted to fit into the straight slots 190 (two foremost slots). Note that the stiffening members 194, 196 are not drawn to scale.

The stiffening members 194, 196 are preferably constructed of a resilient and compressible material. A preferred material is polyurethane foam. The density of the stiffening members 194, 196 may be selected to fine tune the stiffness of the foot 50 to a particular user. In one embodiment, densities of the stiffening members 194, 196 are from 0.4 g/cm$^3$ to 0.6 g/cm$^3$.

The stiffening members 194, 196 preferably provide dampening to the ankle member 52. The stiffening members 194, 196 also alter the rollover characteristics of the foot 50. For a given application, all, some or none of the slots 190 may contain stiffening members 194, 196. If at least some of the slots 190 contain stiffening members 194, 196, one or more of the stiffening members 194, 196 may have different material properties, such as density or compressibility, than one or more of the other stiffening members 194, 196. For example, all the stiffeners 194, 196 on either the lateral or medial side may have a first set of material properties, while the stiffeners 194, 196 on the opposite side have a second set of material properties. More preferably, stiffeners 194, 196 on the medial side may be more compressible than those on the lateral side. This configuration may provide the foot 50 with desirable rollover characteristics, as described in detail below. Of course, stiffeners 194, 196 on opposite sides of the ankle member 52 may have identical material properties.

With reference to FIG. 9, between each of the slots 190, and outside the outermost slots 190, ribs 198 extend generally vertically between the upper and lower surfaces 164, 174 of the ankle member 52. The ribs 198 toward the fore 166 of the foot 50 are substantially straight, while the ribs 198 toward the aft 172 of the foot 50 are curved. The curved ribs 198 are advantageously soft in compression, as they buckle more readily under compressive loads as compared to straight ribs. The ankle member 52 thus provides advantageous cushioning to the wearer. The curved ribs 198 are, however, relatively rigid in tension, providing the foot 50 with durability. Those of skill in the art will appreciate that straight ribs could be substituted for the curved ribs 198, and the ankle member 52 would still provide the advantageous cushioning and durability described above.

With reference to FIGS. 8 and 9, a forward portion 180 of the ankle member 52 includes a split 200. The split 200 extends entirely across the ankle member 52, and diagonally upward and backward from the ankle member lower surface 174. Referring to FIG. 9, the split 200 has a large enough thickness such that surfaces 202, 204 of the ankle member 52 to either side of the split 200 do not abut one another when the ankle member 52 is in a resting state.

A posterior edge 206 of the split 200 adjoins a substantially cylindrical cavity 208 in the ankle member forward portion 180. The cavity 208 extends entirely across the ankle member 52, and provides stress relief to the split 200 The cavity 208 is spaced from the ankle member upper surface 164, from the ankle member lower surface 174, and is positioned forward of the depressions 188 on the ankle member side surfaces. The portion 210 of ankle member 52 material between the cavity 208 and the side surface depressions 188 acts as a hinge during rollover, as described below.

Those of skill in the art will appreciate that the illustrated location and orientation of the split 200 and the cavity 208 is just one possible configuration. For example, the split 200 could be located more posteriorly, perhaps overlapping a middle portion of the ankle member 52. As the position of these features relative to the remainder of the ankle member 52 changes, the rotational response of the foot 50 changes. That is, the location and orientation of the split 200 and the cavity 208 affects the softness or stiffness of the foot 50 as it rotates in the sagittal plane during rollover. This concept is explained more fully below.

Figure 3:
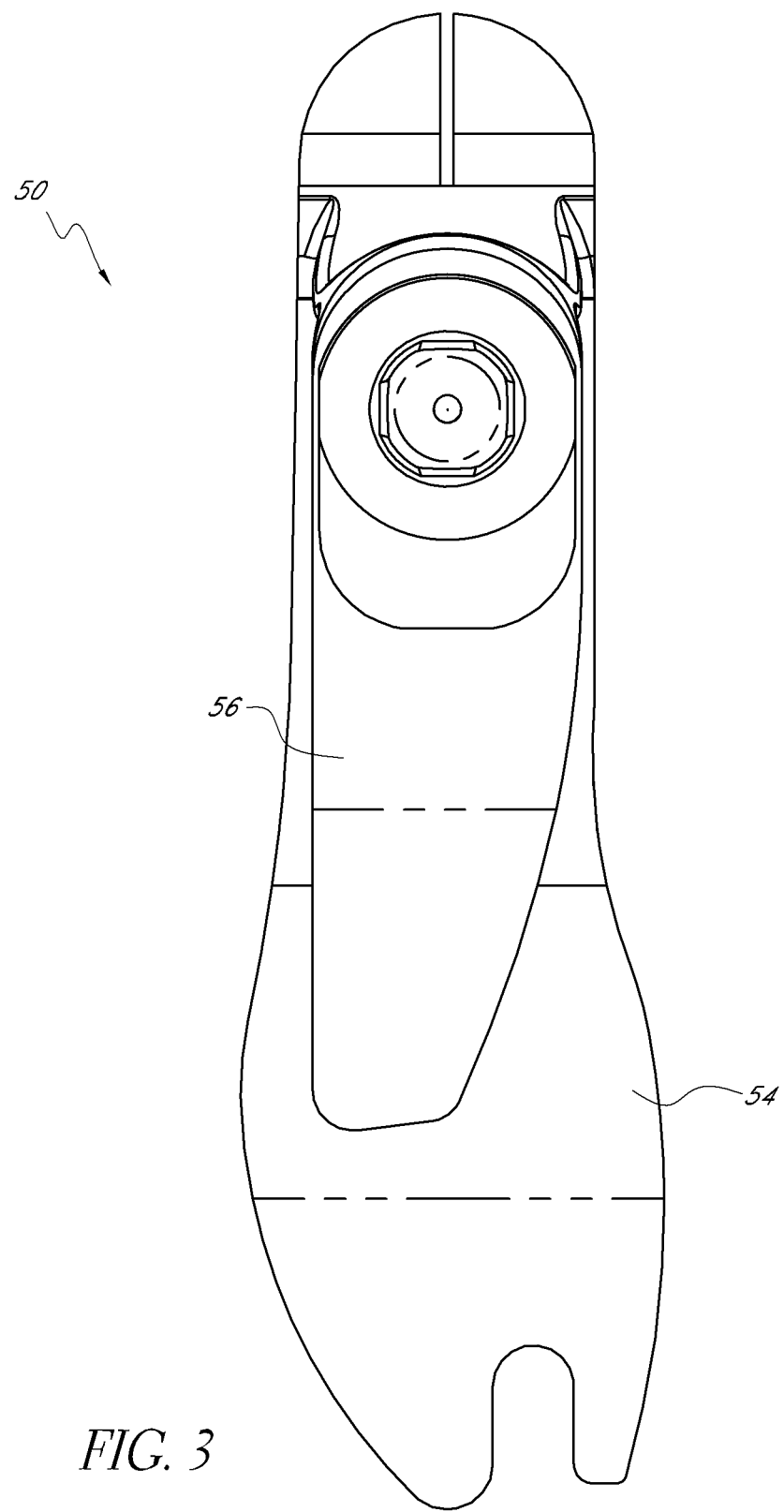
FIG. 3 is a top plan view of the foot prosthesis of FIG. 1.

FIGS. 1-3 illustrate the foot 50 in the assembled configuration, while FIG. 4 illustrates the major components of the foot 50 in an exploded configuration. The ankle member lower surface 174 abuts the foot element upper surface 186, while the ankle member upper surface 164 abuts the upper element lower surface 212. The ankle member 52 is thus sandwiched between the foot element 54 and the upper element 56.

Glue or another bonding agent may secure the upper element 56 and the foot element 54 to the ankle member 52. Alternatively, the ankle member 52 may be directly cast onto the upper element 56 and the foot element 54. In the direct casting process, the material that forms the ankle member 52 is injected into a mold such that the ankle member material directly contacts the foot element upper surface 186 and the upper element lower surface 212. As the ankle member material hardens, it adheres to these surfaces 186, 212. The direct casting method can produce a stronger bond between mating surfaces than glues or other bonding agents.

The bond between abutting surfaces can be strengthened if the solid surfaces are roughened prior to performing the direct casting. For example, the foot element upper surface 186 and the upper element lower surface 212 may be roughened before the ankle member 52 is injected into the mold. One method of roughening these surfaces involves applying a rough weave fabric layer to each surface before the surface is cured. After the surface is cured, the cloth is removed, leaving behind a roughened surface.

A male pyramid adapter 214 resides atop the rear portion 144 of the upper element 56. The adapter 214 is positioned directly above the fillet 78 in the foot element 54. The adapter 214 is illustrated in detail in FIGS. 21-26. The adapter 214 is preferably constructed of metal. In one embodiment, the adapter 214 is constructed of titanium and/or aluminum.

Figure 22:
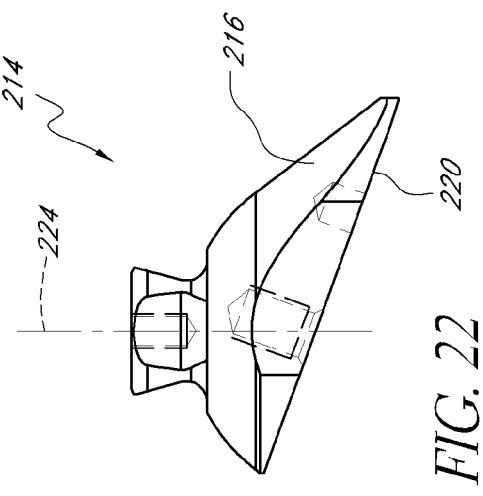
FIG. 22 is a left side elevational view of the adapter of FIG. 21.
Figure 25:
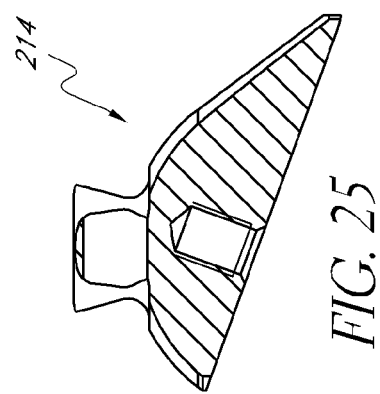
FIG. 25 is a left side sectional view of the adapter of FIG. 21 taken along the line 25-25 in FIG. 23.
Figure 21:
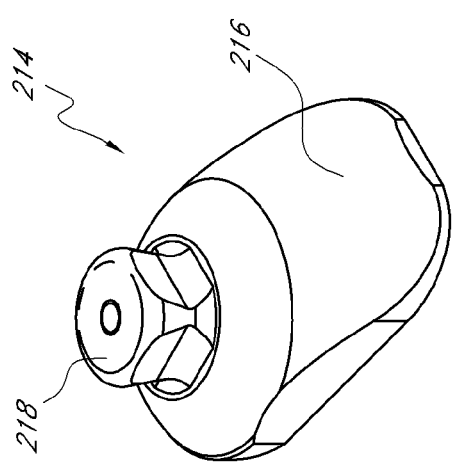
FIG. 21 is a front perspective view of the pyramid adapter of the foot prosthesis of FIG. 1.
Figure 24:
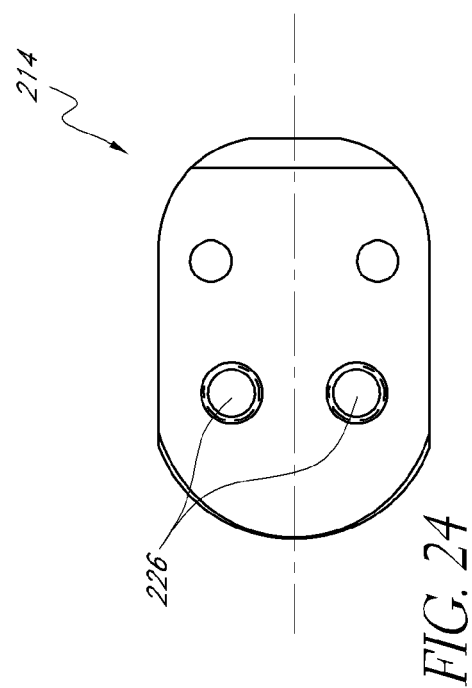
FIG. 24 is a bottom plan view of the adapter of FIG. 21.

With reference to FIG. 21, the adapter 214 comprises a base portion 216 and a mating portion 218. The base portion 216 includes a sloped lower surface 220 (FIG. 22) that sits flush against the sloped upper surface 222 of the upper element 56, as shown in FIG. 2. The remainder of the base portion 216 is shaped so as to present the mating portion 218 in an orientation in which a longitudinal axis 224 of the mating portion 218 is substantially vertical, as shown in FIG. 22.

The lower surface 220 of the base portion 216 includes first and second receiving holes 226 (FIGS. 23 and 24) that align with the first and second holes 162 in the upper element 56 and with the indentations 170 in the upper surface 164 of the ankle member 52. As shown in phantom lines in FIG. 2, shafts 228 of the fastening members 230 (FIG. 4) protrude through the first and second holes 162 in the upper element 56. The protruding shafts 228 engage the receiving holes 226 in the pyramid adapter 214, thus securing the pyramid adapter 214 to the upper element 56. The fastening members 230 may include external threads, and the receiving holes 226 may include internal threads.

The upper element 56 is secured to the upper surface 164 of the ankle member 52 such that the head portion 232 (FIG. 4) of each fastening member 230 seats within one of the indentations 170 in the upper surface 164, as shown in phantom lines in FIG. 2.

With reference to FIGS. 1 and 4, the perimeter of the upper element 56 traces substantially the same path as the perimeter of the ankle member upper surface 164. The upper element 56 is positioned upon the ankle member 52 such that there is substantially no overlap between these two perimeters. The ankle member 52 is positioned upon the foot element 54 such that a fore-to-aft center of the ankle member 52 is positioned rearward of a fore-to-aft center of the foot element 54. With reference to FIG. 3, a side-to-side center of the ankle member 52 is substantially aligned with a side-to-side center of the foot element 54, except in an anterior portion of the ankle member 52, as described below.

Figure 38:
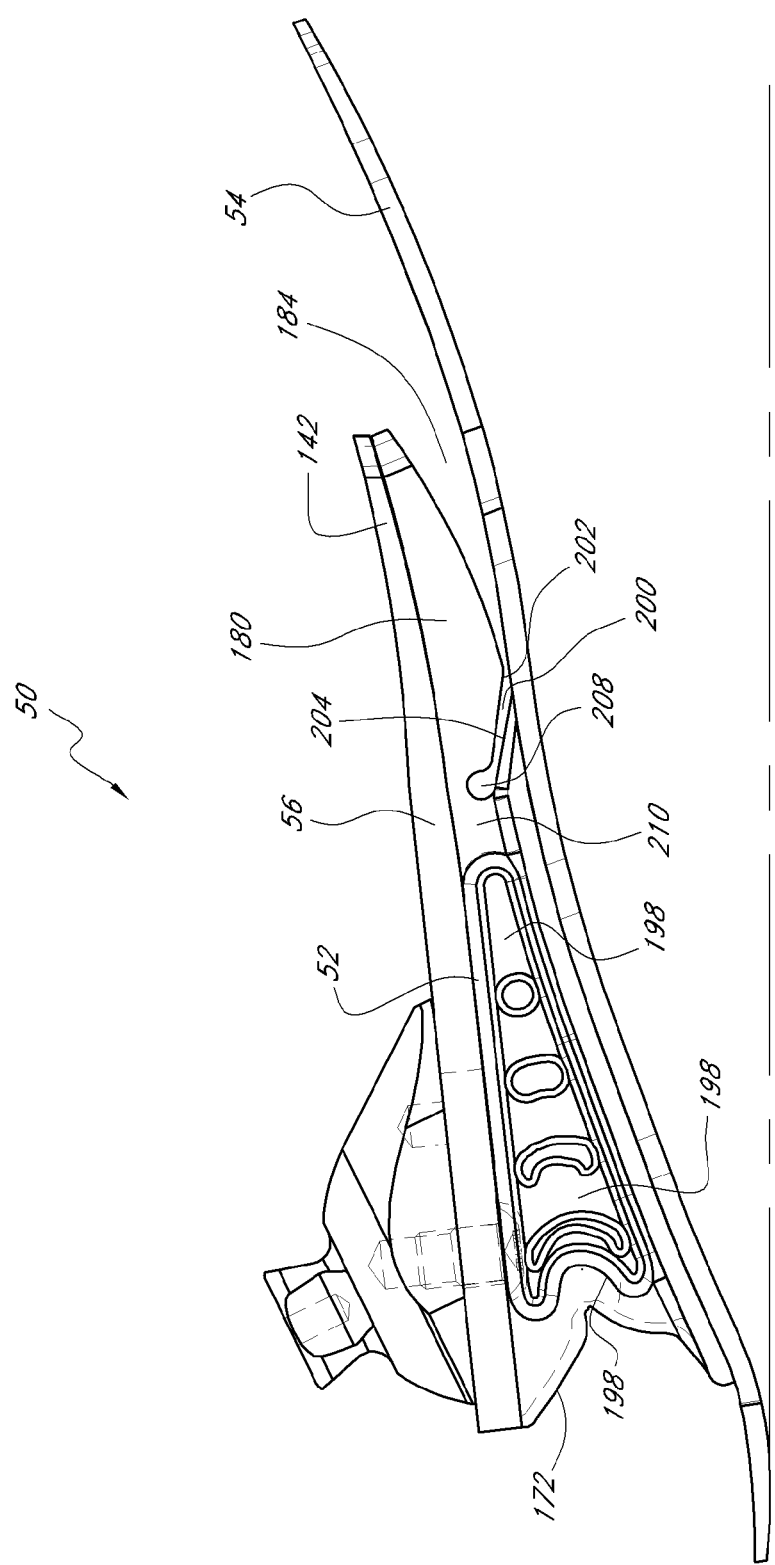
FIG. 38 is a left side elevational view of the foot prosthesis of FIG. 1, illustrating the deformation of the foot at heel strike.
Figure 39:
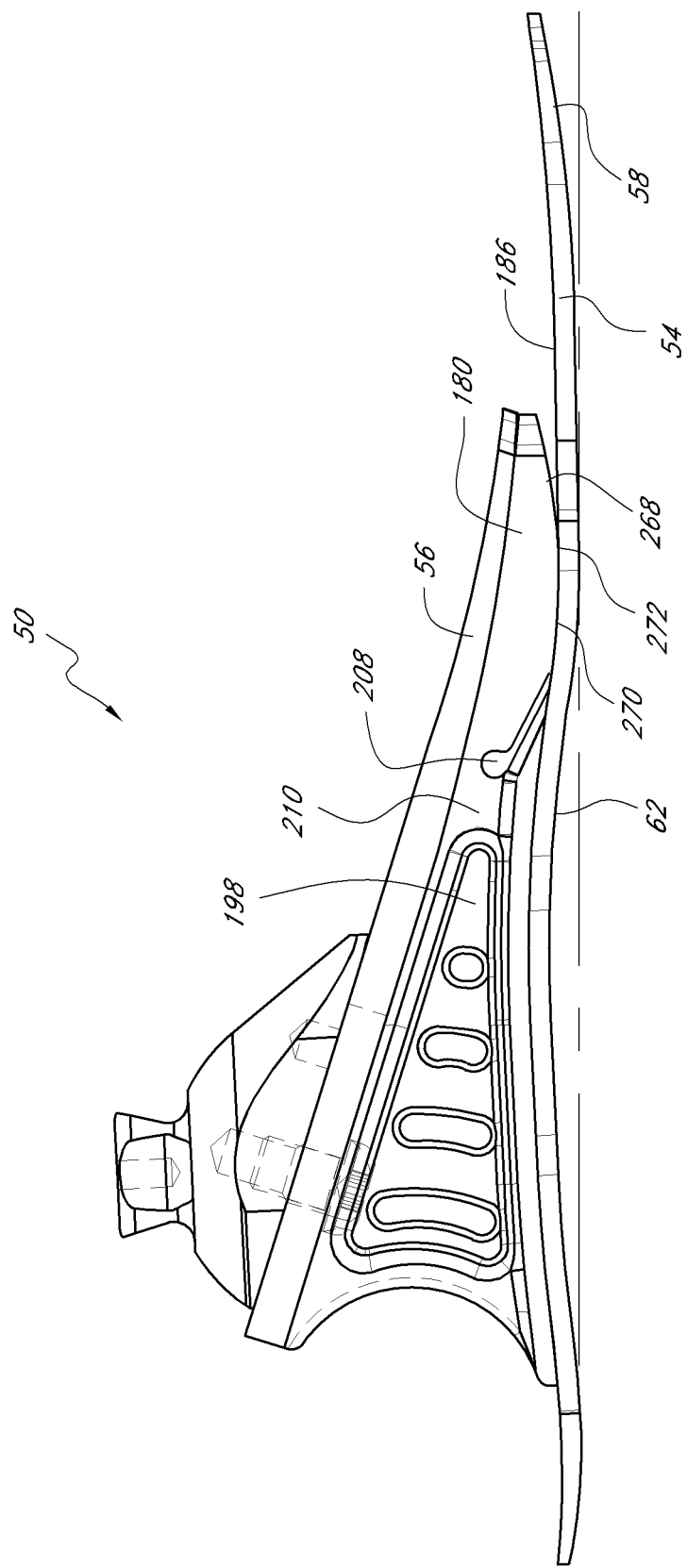
FIG. 39 is a left side elevational view of the foot prosthesis of FIG. 1, illustrating the deformation of the foot at mid stance.
Figure 40:
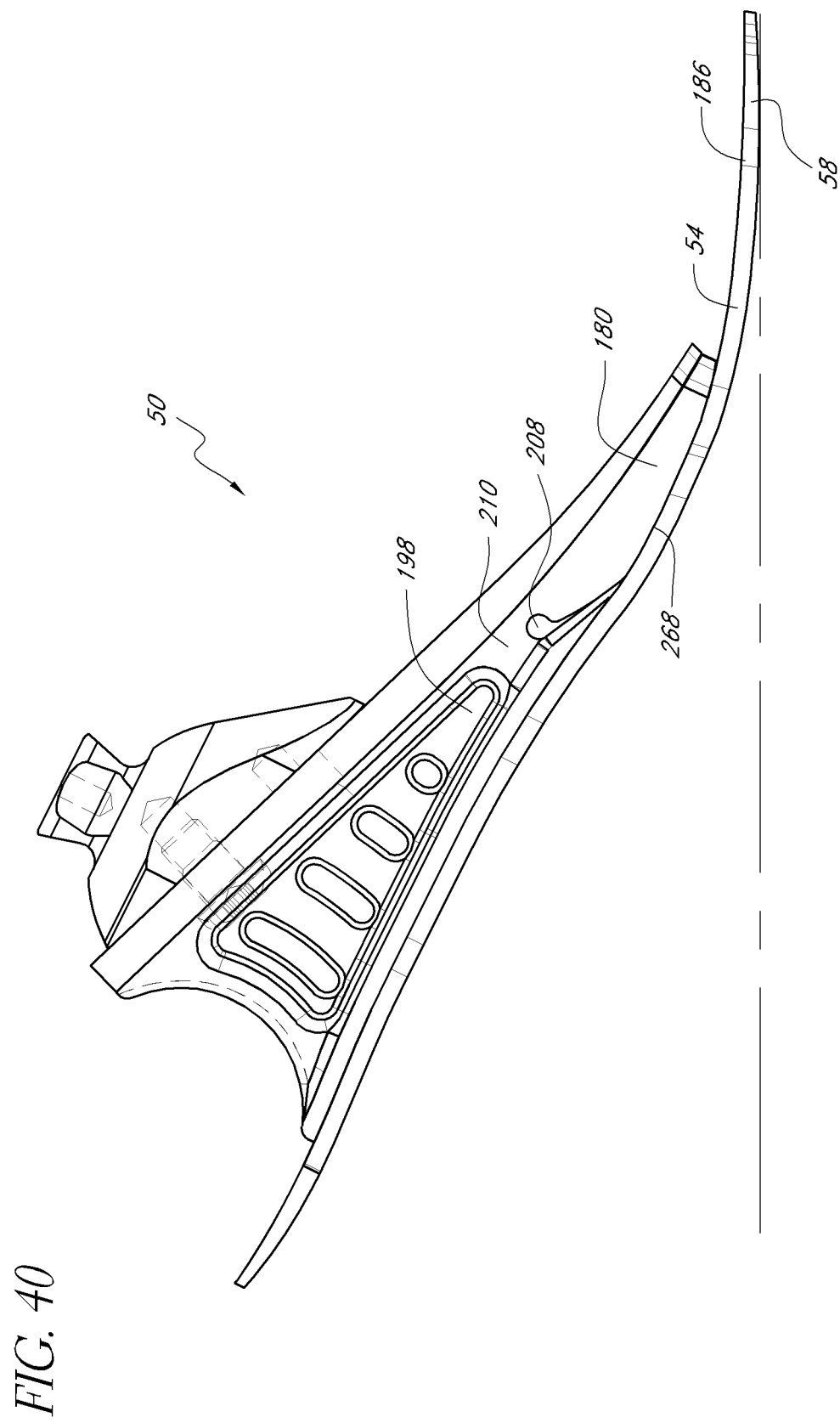
FIG. 40 is a left side elevational view of the foot prosthesis of FIG. 1, illustrating the deformation of the foot at toe off.

FIGS. 38-40 illustrate the foot 50 as it rolls over from heel strike to toe off. Several features of the foot 50 contribute to the advantageous rollover that the foot 50 achieves. For example, at heel strike, illustrated in FIG. 38, the split heel portion 60 stabilizes the foot 50, as described in detail above. Further, the resilient sole 234 at the heel 60 compresses at heel strike. The deformation helps to distribute forces over a wider area, which further enhances stability. This compression continues through the wearer's gait, enhancing stability all the way through.

At heel strike, the curvature and tapered thickness of the foot element heel portion 60 provide comfort and stability enhancement, as described in detail above. With reference to FIG. 38, the heel portion 60 of the foot element 54 bends upward at heel strike. The deforming foot element 54 compresses the posterior portion of the ankle member 52. The concave curvature of the ankle member posterior surface 172, coupled with the curved shape of the aftmost ribs 198, makes the posterior portion softer in compression. Moreover, the relatively greater thickness of the ankle member 52 in the posterior section provides the foot 50 with more compression during heel-strike, while also allowing for additional rotational ability. The ankle member 52 thus provides increased cushioning at heel strike.

The deformation of the posterior portion of the ankle member 52 at heel strike is often so pronounced that the aftmost rib 198 buckles and contacts the next aftmost rib 198, as shown in FIG. 38. The buckling rib 198 collapses the aftmost slot 190. If the load upon the foot 50 is great enough, additional ribs 198 may buckle and additional slots 190 may collapse. The collapsing slots 190 create progressive dampening within the ankle member 52. When the aftmost slot 190 collapses, the stiffness in the ankle member 52 increases due to the increased density of the ankle member 52. When the next aftmost slot 190 collapses, the stiffness in the ankle member 52 increases even further. This progressive dampening advantageously tailors the response characteristics of the ankle member 52 to the wearer.

With continued reference to FIG. 38, the lack of attachment between the anterior portion 142 of the upper element 56 and the foot element 54 eliminates pull in this area during heel strike. The anterior portion 142 of the upper element 56 is not constrained from moving away from the foot element 54. The compression of the posterior portion of the ankle member 52 at heel strike thus generates no tension in the anterior portion 180 of the ankle member 52, which in turn allows the posterior portion to compress further. This feature further enhances the cushioning capability of the foot 50. The shape, orientation and location of the gap 200 between the facing surfaces 202, 204 of the ankle member anterior portion 180 affects the heel stiffness of the foot 50. Likewise, the shape, orientation and location of the gap 184 between the ankle member anterior portion 180 and the foot element 54 affects the heel stiffness of the foot 50.

At mid stance, illustrated in FIG. 39, several features of the foot 50 begin to guide the foot's center of mass inward, toward the medial side of the foot 50. For example, if the foot 50 includes the functional sole 234 described above, the relatively soft material 246 at the ball of the foot element 54 tends to deform and compress more than the relatively more firm material 236 surrounding the soft material 246. The medial location of the softer material 246 guides the foot's center of mass inward.

The asymmetrical upper element 56 further enhances the medially-guided rollover. With reference to FIGS. 3 and 20, the medial edge 158 of the upper element 56 tapers toward its lateral side from approximately the lengthwise midpoint of the element 56 toward the anterior edge 154 thereof. With reference to FIGS. 4 and 10, the upper surface 164 of the ankle member 52 shares this perimeter shape. Thus, the ankle member 52 provides greater support for the wearer's weight on the lateral side. As the wearer's gait progresses forward, this uneven weight support guides the foot's center of mass medially, as the foot element is allowed to flex more toward its medial side due to the lack of an overlying ankle member and upper element. The curved taper of the upper element 56 and the ankle member 52 gradually guides the foot's center of mass farther and farther medially as the wearer's gait progresses toward toe off.

The addition of stiffening members 194, 196 to the ankle member 52 may further enhance the guided rollover. For example, a stiffener or stiffeners 194, 196 that is/are relatively firm may be positioned within the slot(s) 190 on the lateral side of the ankle member 52, while a stiffener or stiffeners 194, 196 that is/are relatively soft may be positioned within the slot(s) 190 on the medial side. Alternatively, a stiffener or stiffeners 194, 196 may be positioned within the slot(s) 190 on the lateral side of the ankle member 52, while no stiffeners are positioned within the slot(s) 190 on the medial side. In either case, the lateral side of the ankle member 52 is less compressible than the medial side. As the foot 50 rolls over, the greater compressibility of the medial side further guides the foot's center of mass inward.

FIG. 41 illustrates the advantageous guided rollover that the present foot 50 achieves. FIG. 41 is a scan of the pressure applied by the foot 50 to a walking surface as the foot 50 rolls over from heel strike to toe off. The image on the right maps the pressure applied by the foot 50, while the image on the left maps the pressure applied by the wearer's natural left foot. The dots in each image follow the path of the center of pressure as it travels through rollover. To mimic the path followed by a natural human foot, this center of pressure preferably starts at the center of the heel and travels in a substantially straight line until it reaches approximately the ball of the foot. It then preferably curves medially and continues toward the wearer's first and second toes. Preferably, the distance between each of the dots is substantially uniform, indicating a smooth rollover with no abrupt changes in speed.

The scan on the right, which follows the path of the center of pressure of the present foot 50, indicates that the present foot 50 provides an advantageous rollover. The dots are substantially uniformly spaced. The dots start at the center of the heel and travel in a substantially straight line until they reach approximately the ball of the foot. They then curve medially and continue toward the wearer's first and second toes.

FIGS. 28-37 illustrate several alternative embodiments that achieve the guided rollover described above. For example, the embodiments of FIGS. 28-31 and 35-37 include uniquely designed foot elements 88, 90, 92, 120, 122, 132. Each of these embodiments is described in detail above, and the descriptions will not be repeated here.

Figure 32:
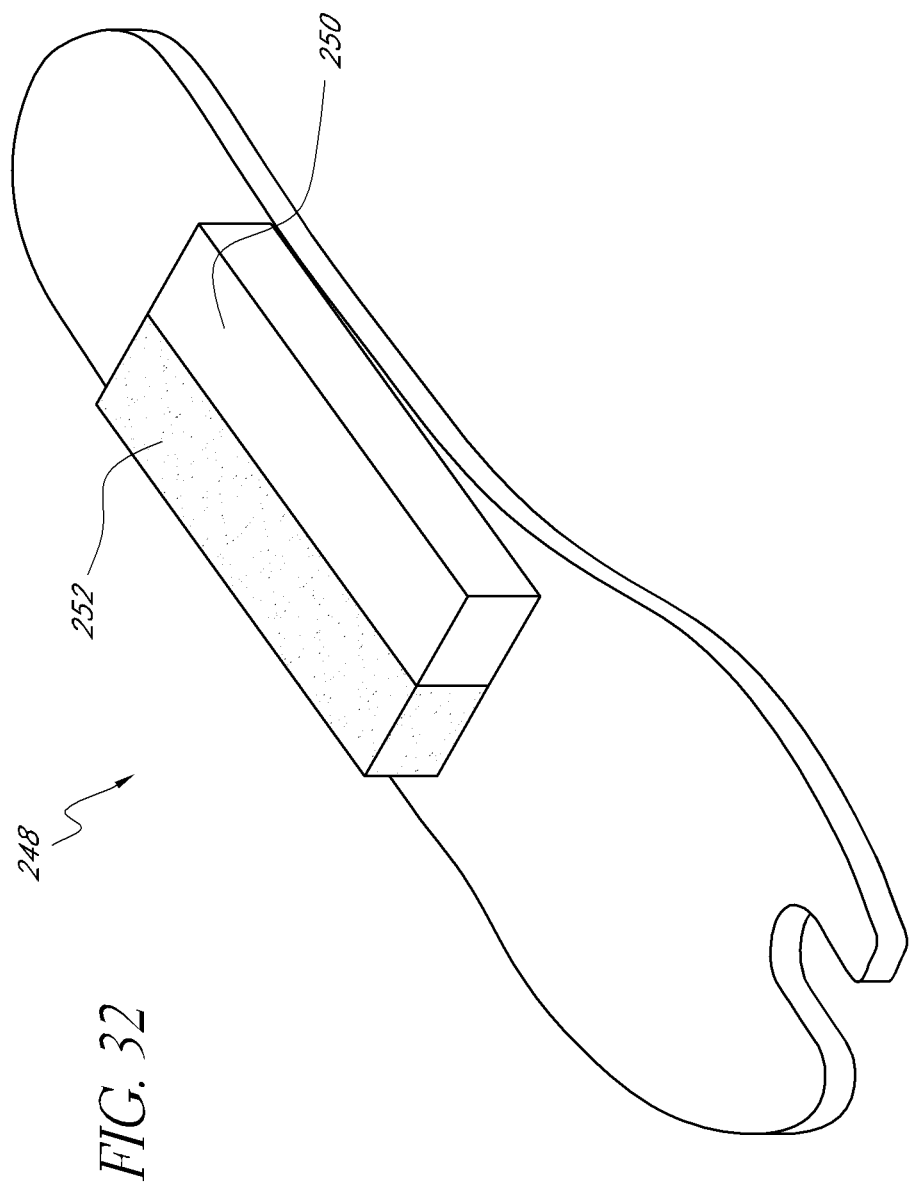
FIG. 32 is a front perspective view of another alternative foot element.

FIG. 32 illustrates, schematically, a conceptual design for an ankle member 248 that achieves the guided rollover described above. The ankle member 248 comprises a medial portion 250 and a lateral portion 252. The medial and lateral portions 250, 252 have different stiffnesses. For example, the medial and lateral portions 250, 252 could be constructed of different densities of the same material, or they could be constructed of entirely different materials. In one embodiment, the medial portion 250 has a softer stiffness than the lateral portion 252. With a softer stiffness on the medial side, the medial portion 250 compresses more than the lateral portion 252 as the ankle member 248 rolls over, thus guiding the foot's center of mass inward. To guide the foot's center of mass outward (toward the lateral side), the medial portion 250 may have a greater stiffness than the lateral portion 252.

Another alternative ankle member (not shown) includes anterior and posterior portions. The anterior and posterior portions have different stiffnesses. In one embodiment, the anterior portion has a softer stiffness than the posterior portion. In another embodiment, the anterior portion has a greater stiffness than the posterior portion.

Another alternative ankle member (not shown) comprises a unitary member with areas of different stiffness or density. For example, the ankle member may include various layers, with some layers having different stiffness than other layers. Alternatively, the ankle member could comprise a matrix of a first stiffness with pockets or plugs of a second stiffness.

Figure 33:
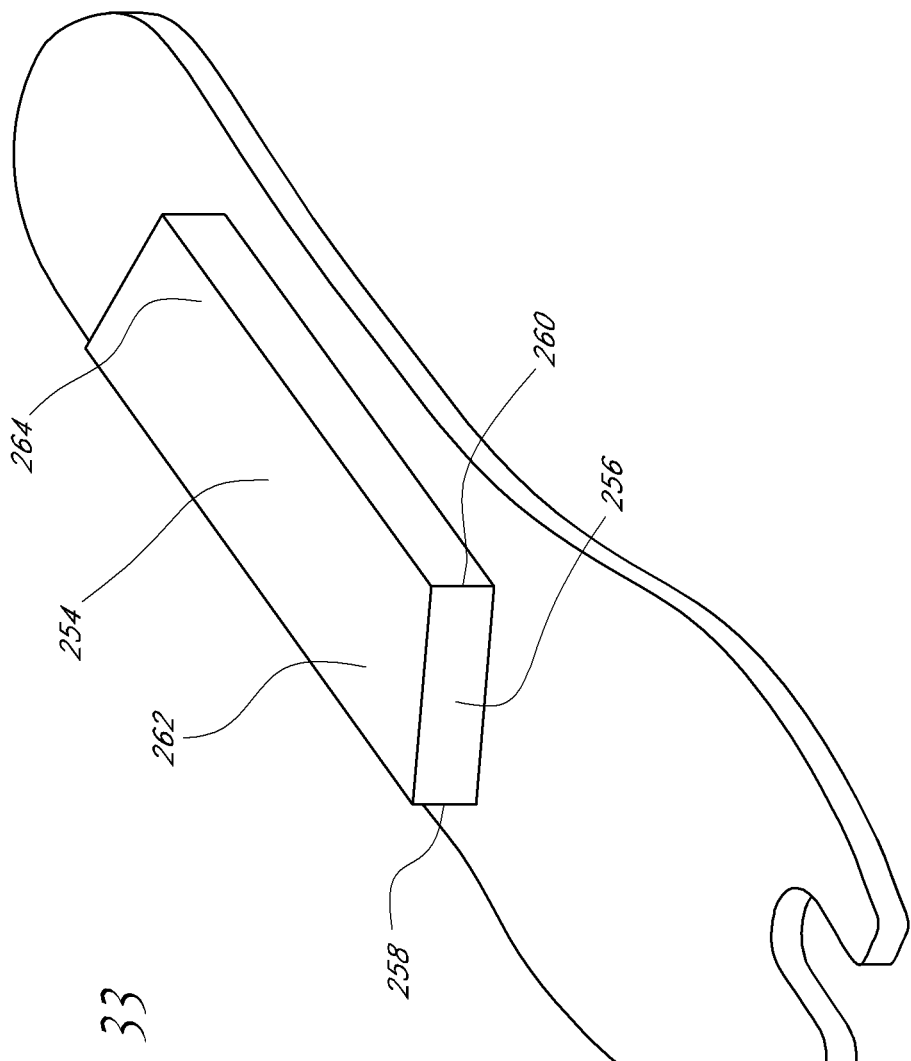
FIG. 33 is a front perspective view of another alternative foot element.

FIG. 33 illustrates, schematically, another conceptual design for an ankle member 254 that achieves the guided rollover described above. The ankle member 254 is shaped substantially as a rectangular parallelepiped having a diagonally truncated anterior surface 256. Thus a lateral anterior edge 258 of the ankle member 254 extends farther forward than a medial anterior edge 260. As the ankle member 254 rolls over from mid stance to toe off, the lateral side 262 of the ankle member 254 supports more and more of the wearer's weight, thus guiding the foot's center of mass inward. To guide the foot's center of mass outward (toward the lateral side), the configuration of the ankle member 254 may be altered such that the medial anterior edge 260 extends farther forward than lateral anterior edge 258.

These embodiments may be constructed of a single material, or medial and lateral sides of the ankle member 254 may be constructed of different materials. For example, a medial side 264 of the ankle member 254 may be constructed of a softer material than the lateral side 262, or vice versa.

Figure 34:
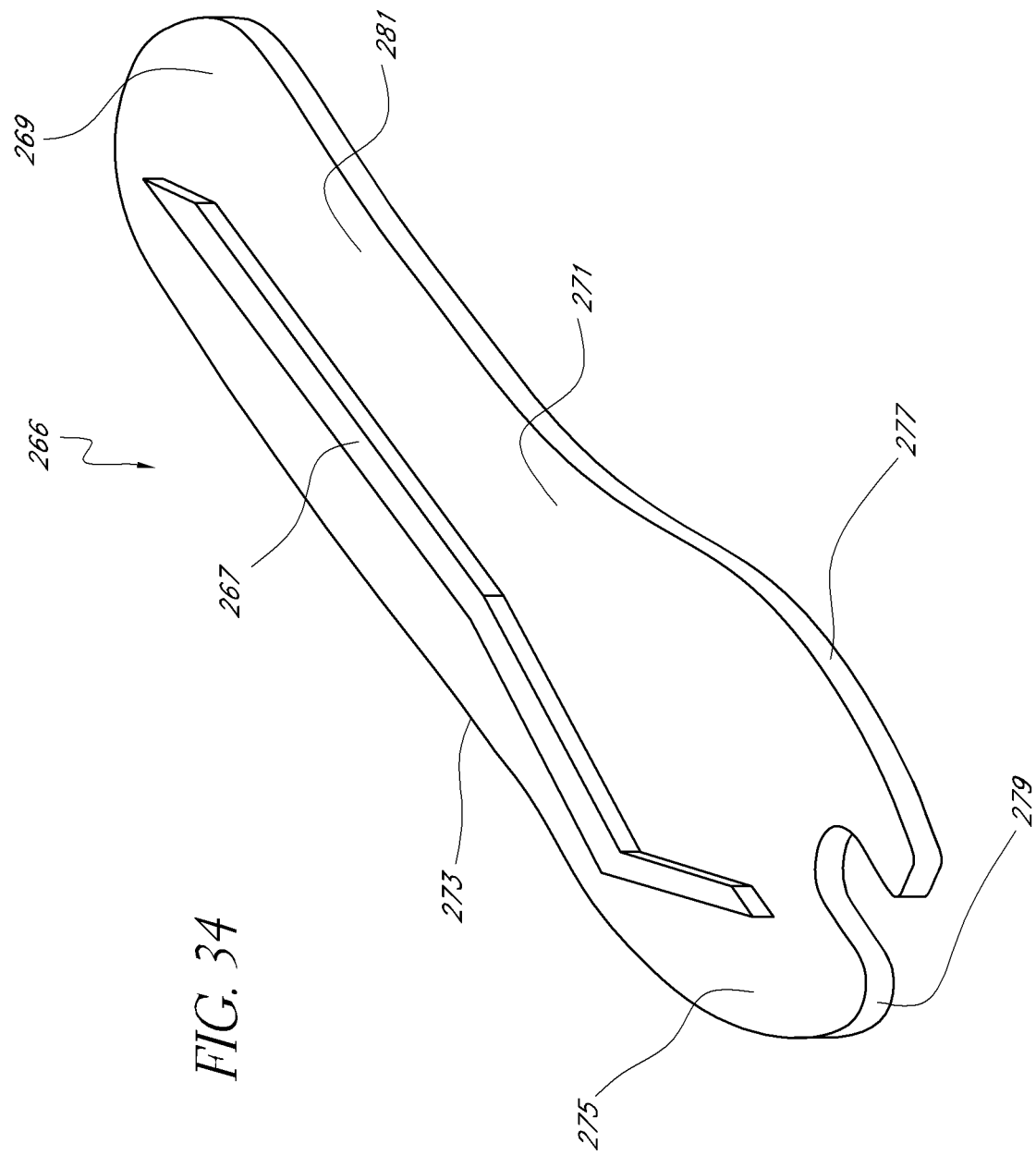
FIG. 34 is a front perspective view of another alternative foot element.

FIG. 34 illustrates, schematically, a conceptual design for a foot element 266 that achieves the guided rollover described above. The foot element 266 includes a strip 267 where the foot element 266 has an increased thickness. In the illustrated embodiment, the strip 267 runs from a heel portion 269 of the foot element 266 substantially straight forward to an arch portion 271 thereof. This portion of the strip 267 runs substantially parallel to a longitudinal axis of the foot element 266, and is positioned laterally of the longitudinal axis. The strip 267 then turns slightly toward the lateral side 273 of the foot element 266 and continues diagonally forward into a toe portion 275 thereof. The strip 267 then turns back toward the medial side 277 of the foot element 266 and continues diagonally forward before terminating short of an anterior edge 279 thereof.

The location and shape of the strip 267 contribute to guiding the foot's center of mass inward as the foot 50 rolls over. The increased effective thickness of the foot element 266 increases the stiffness thereof in the region of the strip 267. Thus, in the heel and arch portions 269, 271, the stiffness of the foot element 266 is greater on the lateral side 273. As the strip 267 turns toward the lateral side 273, the width of the foot element 266 increases. The positioning of the strip 267 farther and farther toward the lateral side 273 of a progressively wider foot element 266 increases the tendency of the foot's center of mass to be guided toward the medial side 277.

The strip 267 may be formed as a separate component that is secured to the upper surface 281 of the foot element 266. Alternatively, the foot element 266 and the strip 267 may be formed as a unitary piece. If the strip 267 is formed as a separate component, it may be constructed of a different material than the foot element 266, or it may be constructed of the same material.

As FIG. 39 illustrates, the curvature of the arch portion 62 of the foot element 54 flattens as the wearer's gait reaches mid stance. The deformation of the foot element 54 provides further cushioning to the wearer. Further, as the wearer's gait passes through mid stance the resilient foot element 54 begins to return to its natural shape, thus providing energy return to the wearer. As the foot passes through mid-stance, the gap 184 beneath the ankle member 52 closes, such that the user now takes advantage of substantially the entire compressive ability of the ankle member 52.

As the wearer's gait transitions from mid stance to toe off (FIGS. 39 and 40), the toe portion 58 of the foot element 54 flexes, thus decreasing a radius of curvature of the toe portion 58. The more the gait progresses toward toe off, the more the foot element 54 flexes. As the foot element 54 flexes, its upper surface 186 moves closer to the lower surface 268 of the anterior portion 180 of the ankle member 52. A contact area 270 (FIG. 39) between these two surfaces 186, 268 gradually increases as an anterior edge 272 of the contact area 270 gradually moves forward. At toe off (FIG. 40), the entire lower surface 268 of the anterior portion 180 of the ankle member 52 contacts the foot element upper surface 186. This progressively increasing support surface area 270 provides increased stability from mid stance to toe off.

The anterior edge 272 of the contact area 270 acts as a fulcrum, and the foot element 54 pivots about this fulcrum. Because the anterior edge 272 travels forward as the wearer's gait approaches toe off, the lever arm of the foot element toe portion 58 gradually decreases in length through this portion of the wearer's gait. The decreasing lever arm length increases the effective stiffness of the foot element toe portion 58. Thus, the toe portion 58 gradually provides increasing energy return from mid stance to toe off, resulting in a smooth rollover.

The outwardly bulging lateral edge 66 in the toe portion 58 contributes to a more natural toe off. As discussed in detail above, the unique configurations of the upper element 56 and the ankle member 52 contribute to guiding the foot's center of mass inward as the foot 50 rolls over. The outwardly bulging lateral edge 66 also contributes to this beneficial effect. Because the lateral edge 66 bulges outwardly, it provides leverage for urging the center of mass medially as the foot 50 rolls toward toe off.

With reference to FIGS. 38-40, the solid material area 210 between the cylindrical cavity 208 and the foremost rib 198 acts as a hinge through the wearer's gait. At heel strike (FIG. 38), the material posterior to the hinge 210 is in compression. The foot element 54 and upper element 56 pivot about the hinge 210 to compress the posterior portion of the ankle member 52. The material anterior to the hinge 210 is not in tension, due to the lack of connection between the anterior portion 142 of the upper element 56 and the foot element 54.

As the foot 50 rolls forward to mid stance, the elements 54, 56 pivot in the opposite direction to achieve the configuration of FIG. 39. And as the foot 50 rolls forward toward toe off, the elements 54, 56 continue to pivot in the same direction about the hinge 210, closing the gap 184 at the anterior of the ankle member 52 and placing the posterior portion of the ankle member 52 in tension. The relatively long upper element 56 reduces tearing forces between the upper element 56 and the posterior portion 168 of the ankle member 52. Thus, this configuration increases the durability of the foot 50.

The location of the hinge 210 affects the heel stiffness and the rotational response of the foot 50. As the hinge 210 moves more posteriorly, the heel becomes softer. As the hinge 210 moves more anteriorly, the heel becomes stiffer.

The foot 50 illustrated in FIGS. 1-4 is adapted to substitute for a natural right human foot. Those of skill in the art will appreciate that a foot configured as a mirror image about a longitudinal axis of the illustrated foot 50 would be adapted to substitute for a natural left human foot. For example, the foot element 54 illustrated in FIGS. 5-7 has such a mirror image configuration. The illustrated foot 50 and its various components are not intended to limit the scope of the claims that follow to any particular configuration that is adapted for use as a left or right foot.

Figure 42:
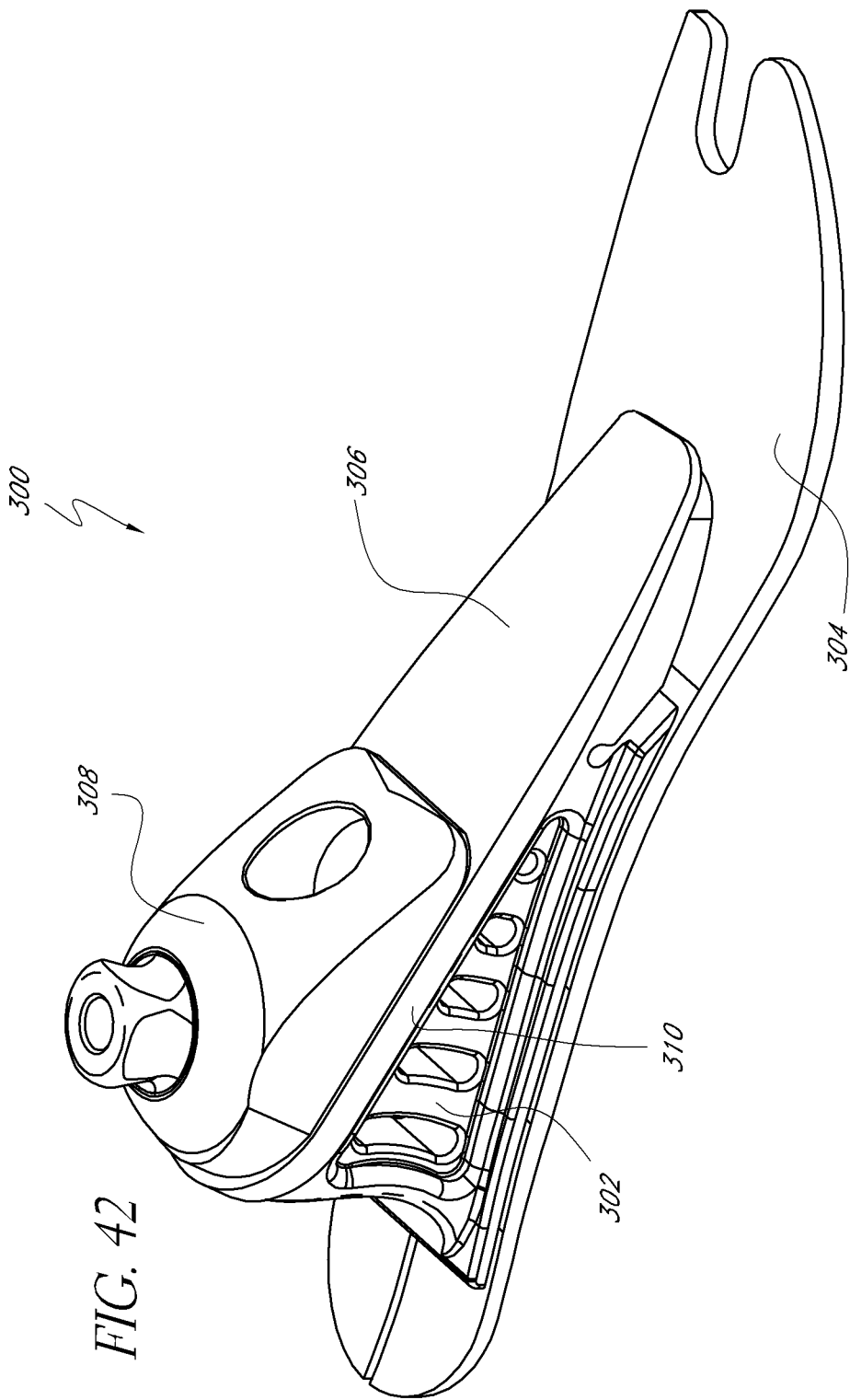
FIG. 42 is a front perspective view of another preferred embodiment of the present foot prosthesis with resilient multi-axial ankle.

FIGS. 42-46 illustrate another embodiment of the present foot prosthesis 300. With reference to FIG. 42, the illustrated foot prosthesis 300 comprises a resilient ankle member 302 sandwiched between a lower element 304, or foot element 304, and an upper element 306 or ankle element 306. The ankle member 302, lower element 304 and upper element 306 are similar to the corresponding elements of the foot 50 illustrated in FIG. 1.

A male pyramid adapter 308 resides atop a rear portion 310 of the upper element 306. The adapter 308, which is similar to the adapter 214, is illustrated in greater detail in FIGS. 43-46. The adapter 308 includes a through-bore 312 in a forward portion 314 thereof (FIG. 43). A longitudinal axis of the through-bore 312 is perpendicular to a plane defined by the rear portion 310 (FIG. 45) of the upper element 306. The through-bore 312 advantageously reduces the weight of the adapter 308, which in turn reduces the weight of the entire foot 300. Those of skill in the art will appreciate that the adapter 308 need not include the through-bore 312.

With reference to FIG. 45, a lower end of the through-bore 312 includes a plug 316. In the illustrated embodiment, the plug 316 is substantially disk-shaped, such that it covers an entire area of the upper element 306 that would otherwise be exposed by the through-bore 312. In the illustrated embodiment, the plug 316 is about half as thick as the rear portion 310 of the upper element 306. However, those of skill in the art will appreciate that the plug 316 could be thinner or thicker.

The plug 316 preferably comprises a resilient material, such as polyurethane. The plug 316 serves a variety of functions. For example, the plug 316 aids in securing the adapter 308 to the upper element 306. During one preferred process of constructing the foot 300, described in greater detail below, the material that forms the plug 316 flows into a gap 318 that exists between the forward portion 314 of the adapter 308 and the upper surface 320 of the upper element 306. U.S. patent application Ser. No. 10/642,125, filed on Aug. 15, 2003, discloses further details of a prosthetic foot having a gap between an attachment adapter and an upper element. The gap in the '125 application may or may not receive a resilient material.

With reference to FIGS. 45 and 46, in the illustrated embodiment, the gap 318 is substantially wedge-shaped, becoming wider toward a front edge 322 of the adapter 308. The shape of the gap 318 results from the contour of the lower edge 324 of the forward portion 314, which preferably curls upward toward the front edge 322. This shape enables the upper element 306 to flex more naturally.

As the prosthesis wearer moves about, at least the forward portion 326 of the upper element 306 tends to flex. The greatest amount of flexion occurs at the toe-off phase of gait. The curled shape of the front lower edge 324 of the adapter 308 preferably mimics the curved shape that the upper element 306 achieves as it flexes. Thus, the front lower edge 324 avoids the creation of a stress concentration in the upper element 306. For example, if the front lower edge 324 didn't curl upwardly, and instead resembled a ninety-degree corner at the intersection of the front surface 322 and the lower surface 328 (FIG. 46), that sharp corner would create a fulcrum about which the front portion 326 of the upper element 306 would flex. The fulcrum would inhibit the natural flexing motion of the upper element 306, causing the material in the vicinity of the fulcrum to flex more than it otherwise would, and to flex about a relatively sharp fulcrum. This unnatural motion would create a stress concentration in the upper element 306 that could cause the upper element 306 to fail.

In one embodiment of the present foot prosthesis 300 (the empty gap embodiment), the gap 318 contains no solid material. In this embodiment, nothing impedes the natural flexing of the upper element 306. However, in the illustrated embodiment (the filled gap embodiment), the gap 318 contains resilient material, such as polyurethane. In this embodiment, as the upper element 306 flexes, the gap 318 shrinks. As the gap 318 shrinks, the resilient material in the gap 318 compresses. This compression provides resistance to the flexing of the upper element 306.

In both the empty gap and filled gap embodiments, the gap 318 affects the rollover properties of the foot 300. In the empty gap embodiment, rollover is softest. In the filled gap embodiment, rollover is generally stiffer than the empty gap embodiment, with the stiffness increasing as the compressibility of the gap-filling material decreases.

The adapter 308 may be secured to the upper element 306 in a fashion similar to that described above with respect to the adapter 214 and the upper element 56 of FIG. 4. For example, with reference to FIG. 45, one or more bolts 330 may secure the adapter 308 to the upper element 306. In the filled gap embodiment, the resilient material advantageously reduces stresses in the bolts 330 as the upper element 306 flexes. For the filled gap embodiment, testing has shown a 20%-30% decrease in the stresses formed in the bolts as compared to the empty gap embodiment.

In one embodiment of a method to construct the filled-gap embodiment, a barrier (not shown), such as an o-ring, is placed around a lower portion 332 (FIG. 45) of the adapter 308 after the adapter 308 is secured to the upper element 306. Resilient material in liquid form is then poured into the through-bore 312. The resilient material seeps through a narrow opening 334 (FIG. 46) between the adapter front portion 314 and the upper surface 320 of the upper element 306. The resilient material fills the gap 318. The barrier prevents the resilient material from flowing outward any further. Once the resilient material has cooled and hardened, the barrier is removed.

As explained above, the adapter 308 need not include the through-bore 312. In an embodiment of the foot 300 that does not include the through-bore 312, the resilient material may be applied to the gap 318 in alternative ways, such as by injecting it directly into the gap 318 from the front of the adapter 308.

SCOPE OF THE INVENTION

The above presents a description of the best mode contemplated for carrying out the present foot prosthesis with resilient multi-axial ankle, and of the manner and process of making and using it, in such full, clear, concise, and exact terms as to enable any person skilled in the art to which it pertains to make and use this foot prosthesis. This foot prosthesis is, however, susceptible to modifications and alternate constructions from that discussed above that are fully equivalent. Consequently, this foot prosthesis is not limited to the particular embodiments disclosed. On the contrary, this foot prosthesis covers all modifications and alternate constructions coming within the spirit and scope of the foot prosthesis.

What is claimed is:

1. A prosthetic foot comprising:
   an elongate foot element extending from a proximal end to a distal toe portion;
   the toe portion comprising a cut-out portion defined by two longitudinal edges and a transverse edge that extends between the two longitudinal edges at an anterior end, wherein the cut-out portion is positioned toward a medial side of a longitudinal axis of the foot element; and
   the foot element further comprising a lengthwise split extending along at least a portion of a length of the foot element, wherein the lengthwise split runs substantially straight in an anterior/posterior direction to a distal end of the elongate foot element such that the split is laterally spaced apart from the cut-out portion, a width of the cut-out portion being greater than a width of the split.

2. The prosthetic foot of claim 1, wherein the foot element comprises an arch portion between the proximal end and the distal toe portion.

3. The prosthetic foot of claim 1, wherein the cut-out portion is generally U-shaped.

4. The prosthetic foot of claim 1, wherein the cut-out portion is configured to receive a strap of a sandal.

5. The prosthetic foot of claim 1, wherein the cut-out portion is defined along an axis parallel to an axis of the lengthwise split.

6. The prosthetic foot of claim 1, wherein the lengthwise split extends along a longitudinal axis of the foot element.

7. The prosthetic foot of claim 1, wherein the lengthwise split extends from the distal end of the foot element to a point distal of a posterior end of the foot element.

8. A prosthetic foot comprising:
   an elongate foot element extending from a proximal end to a distal toe portion;
   the toe portion comprising a cut-out portion defined by two longitudinal edges and a transverse edge that extends between the two longitudinal edges at an anterior end, wherein the cut-out portion is positioned toward a medial side of a longitudinal axis of the foot element; and
   the foot element further comprising a lengthwise split extending along at least a portion of a length of the foot element, wherein the lengthwise split runs substantially straight in an anterior/posterior direction toward a distal end of the elongate foot member such that an axis of the lengthwise split is parallel to an axis of the cut-out portion, a width of the cut-out portion being greater than a width of the split.

9. The prosthetic foot of claim 8, wherein the split extends to a base of the cut-out portion.

10. The prosthetic foot of claim 8, wherein the split is laterally spaced apart from the cut-out portion.

11. The prosthetic foot of claim 8, wherein the split extends to a distal end of the foot element.

12. The prosthetic foot of claim 8, wherein the cut-out portion is generally U-shaped.

13. The prosthetic foot of claim 8, wherein the cut-out portion is configured to receive a strap of a sandal.

* * * * *